US009517188B2

(12) United States Patent
Crane et al.

(10) Patent No.: US 9,517,188 B2
(45) Date of Patent: *Dec. 13, 2016

(54) WATER-BASED GEL COSMETIC COMPOSITIONS CONTAINING EMULSIFIER

(71) Applicant: L'OREAL, Paris (FR)

(72) Inventors: Christine Marie Crane, Watchung, NJ (US); Angeles Fonolla-Moreno, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/221,646

(22) Filed: Mar. 21, 2014

(65) Prior Publication Data
US 2015/0265504 A1 Sep. 24, 2015

(51) Int. Cl.
A61Q 1/10 (2006.01)
A61K 8/37 (2006.01)
A61K 8/81 (2006.01)
A61K 8/04 (2006.01)
A61K 8/34 (2006.01)
A61K 8/86 (2006.01)
A61K 8/895 (2006.01)
A61K 8/891 (2006.01)
A61K 8/892 (2006.01)
A61K 8/46 (2006.01)
A61K 8/893 (2006.01)
A61K 8/894 (2006.01)

(52) U.S. Cl.
CPC ............. A61K 8/042 (2013.01); A61K 8/342 (2013.01); A61K 8/375 (2013.01); A61K 8/463 (2013.01); A61K 8/8158 (2013.01); A61K 8/86 (2013.01); A61K 8/891 (2013.01); A61K 8/892 (2013.01); A61K 8/893 (2013.01); A61K 8/894 (2013.01); A61K 8/895 (2013.01); A61Q 1/10 (2013.01); A61K 2800/43 (2013.01); A61K 2800/48 (2013.01); A61K 2800/594 (2013.01); A61K 2800/872 (2013.01)

(58) Field of Classification Search
None
See application file for complete search history.

(56) References Cited

U.S. PATENT DOCUMENTS

| 3,915,921 A | 10/1975 | Schlatzer, Jr. |
| 4,509,949 A | 4/1985 | Huang et al. |
| 4,850,727 A | 7/1989 | Gueret |
| 5,162,410 A | 11/1992 | Sweet |
| 5,236,986 A | 8/1993 | Sakuta |
| 5,412,004 A | 5/1995 | Tachibana et al. |
| 5,811,487 A | 9/1998 | Schulz, Jr. et al. |
| 5,837,793 A | 11/1998 | Harashima et al. |
| 5,863,886 A | 1/1999 | Tracy et al. |
| 5,948,393 A | 9/1999 | Tomomasa et al. |
| 6,150,445 A | 11/2000 | Bostrom et al. |
| 6,458,390 B1* | 10/2002 | Manelski et al. ............ 424/617 |
| 6,641,823 B2 | 11/2003 | Piot et al. |
| 6,710,022 B1* | 3/2004 | Kwetkat .................. A61K 8/04 510/119 |
| 7,094,842 B2 | 8/2006 | Lennon |
| 7,220,408 B2 | 5/2007 | Decoster et al. |
| 7,790,148 B2 | 9/2010 | Bui et al. |
| 7,879,316 B2 | 2/2011 | Ferrari et al. |
| 8,663,666 B2 | 3/2014 | Morita et al. |
| 9,192,562 B2* | 11/2015 | Bolognini ............ A61K 8/8152 |
| 2003/0118538 A1* | 6/2003 | Krause et al. ............. 424/70.16 |
| 2005/0201961 A1 | 9/2005 | Lu et al. |
| 2006/0034875 A1 | 2/2006 | Nakanishi et al. |
| 2007/0093619 A1 | 4/2007 | Bui et al. |
| 2007/0134283 A1* | 6/2007 | Wang et al. .................. 424/405 |
| 2007/0166257 A1* | 7/2007 | Atis .............................. 424/70.7 |
| 2009/0105353 A1 | 4/2009 | Lorant |
| 2010/0297050 A1 | 11/2010 | Bui et al. |
| 2010/0297051 A1* | 11/2010 | Feuillette ........................ 424/65 |
| 2011/0189117 A1 | 8/2011 | Ferrari et al. |
| 2011/0293550 A1 | 12/2011 | Bui et al. |
| 2015/0079015 A1* | 3/2015 | Bolognini et al. ........... 424/70.7 |

FOREIGN PATENT DOCUMENTS

| EP | 216479 A1 | 4/1987 |
| EP | 874017 A2 | 10/1998 |
| FR | WO 2013087927 A1 * | 6/2013 ............... A61K 8/25 |
| WO | 2004024798 A1 | 3/2004 |
| WO | 2005100444 A1 | 10/2005 |
| WO | 2007054824 A3 | 5/2007 |
| WO | 2011076792 A1 | 6/2011 |

OTHER PUBLICATIONS

U.S. Appl. No. 14/221,646, filed Mar. 21, 2014, Crane et al.
U.S. Appl. No. 14/221,674, filed Mar. 21, 2014, Crane et al.
G. Fonnum, J. Bakke, and F.K. Hansen; Associative thickeners. Part I: Synthesis, rheology and aggregation behavior; Colloid and Polymer Science, Apr. 1993, vol. 271, Issue 4, pp. 380-389; http:/link.springer.com/article/10.1007/BF00657419.
Paint and Coating Testing Manual, 14th Edition of the Gardner-Sward Handbook; J.V. Koleske, Editor, ASTM Manual Series: MNL17, ASTM Publication Code No. (PCN), 28-017095-14, 1916 Race Street, Philadelphia, PA 19103, pp. 268-285.
D. Miller, M. Loffler; Polymeric Thickeners for Personal Care Applications; SOFW-Journal, Dec. 2006, 132, pp. 44-51.

(Continued)

Primary Examiner — Abigail Fisher
(74) Attorney, Agent, or Firm — Oblon, McClelland, Maier & Neustadt, L.L.P.

(57) ABSTRACT

Disclosed are water-based cosmetic compositions comprising a synthetic non-associative thickening polymer, a synthetic associative thickening polymer, an emulsifier, a film forming polymer, and a liquid fatty substance. The ratio of the synthetic non-associative thickening polymer to the synthetic associative thickening polymer is greater than 1:1, or alternatively, said ratio is less than or equal to 1:1.

31 Claims, No Drawings

(56) References Cited

OTHER PUBLICATIONS

D. Miller, M. Loffler; Rheological effects with a hydrophobically modified polymer; Colloids and Surfaces A: Physicochem. Eng. Aspects 2006, 288, pp. 165-169.

M. Loffler, D. Miller; A new pH stable Polymer for Gels and O/W Emulsions; Sofw-Journal, Apr. 2002, 128, 4, pp. 46-52.

I.C. Kulkamp-Guerreiro, T.F. Terroso, E.R. Assumpcao, S.J. Bellitz, R.V. Contri, A.R. Pohlmann, S.S. Guterres; Development and stability of innovative semsolid formulations containing nanoencapsulated lipoic acid for topical use; Journal of Nanoscience and Nanotechnology (2012), 12 (10), pp. 7723-7732.

T. Henning, R. Milbradt, D. Miller; Stabilising special-effects particles [Stabilisierte effektpartikel], COSSMA (2003), 4 (3), pp. 49-49.

N. Kumar, R. Tyagi; Dimeric Surfactants: Promising Ingredients of Cosmetics and Toiletries; Cosmetics 2014, 1, pp. 3-13.

R. Canterbery Pepe, J.A. Wenninger, G.N. McEwen Jr. PhD. J.D.; International Cosmetic Ingredient Dictionary and Handbook, Ninth Edition, 2002, vol. 4, pp. 2930-2936; The Cosmetic, Toiletry, and Fragrance Association, 1101 17th Street, NW, Suite 300, Washington, D.C., 20036-4702, www.ctfa.org.

\* cited by examiner

WATER-BASED GEL COSMETIC COMPOSITIONS CONTAINING EMULSIFIER

TECHNICAL FIELD

The present invention relates to water-based gel cosmetic compositions having a viscosity profile that mimics commercially available anhydrous gel eyeliners.

BACKGROUND OF THE INVENTION

Cosmetic compositions in gel form are desirable as gels are easy to apply, afford a more consistent and precise coverage than liquids and are not as drying to the skin as powders. Water-based cosmetic compositions, in particular face and eyeliner compositions, are desirable as water based cosmetics can be easier to remove, are less likely to clog pores, may afford a less shiny and more natural look and feel, and are less expensive to process when compared to oil or solvent-based compositions. While aqueous cosmetic compositions are known, for example U.S. Pat. No. 6,641,823, these compositions are not gels. Most currently marketed gel eyeliners are anhydrous. They are not ideal as they contain hydrocarbon solvents (typically isododecane) and high volatile silicone fluids (such as cyclopentasiloxane). These anhydrous gels typically suffer from inconsistent wear, smudging and are difficult to remove. They typically are also less fresh and more uncomfortable to wear than water-based compositions. Additionally, water-based compositions are typically less costly to produce and offer a more sustainable environmental platform.

There remains need for a water-based gel cosmetic composition.

The current invention provides water-based gel cosmetic compositions that afford a comparable rheological profile to marketed anhydrous gel formulas. This affords the consumer the convenience of gels (e.g. easy control, precise product pick-up) having the desirable properties of both marketed anhydrous gel formulas (good glide, spreadability, coverage and intensity) and water-based cosmetics (freshness, ease of removal, good wear and comfort).

BRIEF SUMMARY OF THE INVENTION

The present invention relates to a water-based gel cosmetic composition comprising at least one synthetic non-associative thickening polymer, at least one synthetic associative thickening polymer, at least one emulsifier, at least one film forming polymer, and at least one liquid fatty substance, said compositions having a viscosity at low shear rate of from about 2,000 to about 90,000 Pa·s at low shear rate and from about 0.1 to about 3 Pa·s at high shear rate (Method A).

In an embodiment the ratio of the at least one synthetic non-associative thickening polymer to the at least one synthetic associative thickening polymer is greater than 1:1.

In another embodiment, the ratio of the at least one synthetic non-associative thickening polymer to the at least one synthetic associative thickening polymer is less than or equal to 1:1.

Another embodiment of the invention relates to method of making up a keratinous substance, in particular the eyes, but applying to the eye lids the above-described composition.

Another embodiment of the invention relates to a method of improving at least one property selected from freshness, long wear, comfort, gentle application, color intensity, ease of removal, water and/or oil-resistance, adhesion, malleability, setting viscosity and transfer resistance of a gel eyeliner by incorporating in said eyeliner a synthetic non-associative thickening polymer, a synthetic associative thickening polymer, and a film forming polymer.

The composition optionally may include other components appropriate for its intended use such as emollients, pigments, preservatives, neutralizers, vitamins, fillers, waxes, and the like.

DETAILED DESCRIPTION OF THE INVENTION

In the following description of the invention and the claims appended hereto, it is to be understood that the terms used have their ordinary and accustomed meanings in the art, unless otherwise specified. All concentrations are by weight percent on an active basis unless otherwise indicated.

"Aqueous phase" means the phase comprising water as well as such substances of a formulation which, due to their hydrophilic character, can be mixed in and/or dissolved in and/or dispersed in water. The aqueous phase of the composition according to the invention is advantageously a continuous aqueous phase. A "continuous aqueous phase" means that the composition has a conductivity, measured at 25° C., of greater than 23 microSiemens/cm, the conductivity being measured, for example, using an MPC227 conductimeter from Mettler Toledo and an Inlab 730 conductivity measuring cell.

"Associative thickening polymers" or "associative thickeners" are water-soluble or hydrophobic soluble polymers having low to moderate molecular weights (up to about $10^5$ g/mol, herein most typically from about 10,000 g/mol to about 50,000 g/mol) and containing terminal or pendant hydrophobic ends to a hydrophilic backbone, the hydrophobic ends being capable of non-specific hydrophobic association such as those similar to conventional surfactants, and which by itself only slightly increases the viscosity of a composition. Associative thickening polymers are known in the art. See, e.g. U.S. Pat. No. 6,150,445; WO2011/076792; G. Fonnum et al, "Associative Thickeners:Part I: Synthesis, rheology and aggregation behavior", Colloid Polymer Sci. 271:380-389 (1993); Paint & Coating Testing Manual, $14^{th}$ Edition (J V Koleske Ed., 1995), pp. 268-288. A "slight increase" in viscosity in the context of this application means that adding this polymer to an inventive composition (or water) increases the viscosity of the composition (or water) by about 2000 mPa·s to about 50000 mPa·s, more typically by about 5000 mPa·s to about 40000 mPa·s (using Method A).

"Easy removal" means the composition may be substantially removed with a non-harsh remover, such as water and/or with a water-based cleansing solution, and without excessive rubbing.

"Emulsifier or emulsifying surfactant" is a term of art that is well known to those skilled in the art. See, e.g. http://pharmlabs.unc.edu/labs/emulsions/agents.htm. It is a compound that has a hydrophilic part and a lipophilic part ("amphiphilic") and facilitates the dispersion of two mutually insoluble phases, in this case the dispersion of a liquid fatty substance in water.

"High color intensity" means dramatic visual impact of the tint, in this instance, the blackness of the compositions and/or eye lids.

"High shear rate," as measured on a TA Instrument G2 Rheometer with a 20 mm 2° cone in continuous mode ("Method A"), means from 950 s-1 to 1000 s-1.

"Low shear rate," as measured on a TA Instrument G2 Rheometer with a 20 mm 2° cone in continuous mode (Method A,), means from 0 s-1 to 0.15 s-1.

"Non-associative thickening polymers" or "non-associative thickeners" are typically high molecular weight (greater than about $10^5$ g/mol to about $10^8$ g/mol) water soluble polymers having a relatively uniform backbone that lacks hydrophobic modification.

"Synthetic" means synthetically derived.

"Thickener" is term that is well known to a skilled artisan. It means a compound or composition that increases the viscosity or resistance to flow of a composition to which it is added. See, Paint & Coating Testing Manual, 14$^{th}$ Edition (J V Koleske Ed., 1995), pp. 268-288; WO2011/076792. A thickening polymer is thus a thickener that is a polymer.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

Unless otherwise specified herein, all percentages and ratios of components are by weight relative to the total weight of the final composition.

The viscosity of the gels were also measured at 25° C. with a Rheomat 180 viscometer at 200 rmp (revolutions per minute) using a No. 4 or 5 spindle (hereinafter, "Method B"). Using this instrument the viscosity is preferably greater than or equal to 5 Pa·s, preferably from about 5 Pa·s to about 65 Pa·s, most typically about 5 to about 60 Pa·s, including all ranges and subranges therebetween. When the composition includes waxes, the viscosity trends to the higher ranges with the upper range closer to 60 Pa·s. When no waxes are present, the viscosity is lower, with an upper viscosity range closer to about 35 Pa·s The viscosity was measured 10 minutes after switching on the rotation of the spindle.

While the gels of the invention remain pseudoplastic, that is the viscosity of the gels is higher at low shear rate and decreases with increasing shear rate during a steady shear or continuous flow, the use of applicants' dual-agent viscosity increasing system in oil-in-water emulsions or water-based dispersions affords comparable non-Newtonian rheology to that displayed by anhydrous compositions or by compositions having only a single viscosity increasing agent. By displaying this non-Newtonian rheology, the compositions of the invention afford improved setting, reduced sag and enhanced flow during application of the compositions.

The gels of the invention display a particular viscosity ranging from 2,000 Pa·s to 90,000 Pa·s at low shear rate and from 0.01 Pa·s to 3 Pa·s at high shear rate (using Method A) and have slopes from about 0.5 to about 1.0, most preferably 0.6 to about 1.0. The slope referred to herein is the slope of viscosity (Pa·s) versus shear rate (1/s) graph. This viscosity profile is unique in that it affords a water-based gel system that mimics the viscosity profile of several different types of anhydrous gel systems.

In the gels of the invention, the combination of the synthetic associative thickening polymer and the non-associative thickening polymer in a particular ratio, or the associative polymer alone, together with the film forming polymer and the emulsifier unexpectedly increased the viscosity of the resulting composition at low shear by at least 2000 Pa·s as measured on a TA Instrument G2 Reheometer with a 20 mm 2° cone in continuous or steady state mode.

Throughout this application, the shear rate applied to the gels at "low shear" is from about 0.01 s-1 to about 1 s-1. The shear rate applied to the gels at "high shear" is from about 900 s-1 to about 1000 s-1.

The pH of the gels of the invention at 25° C. ranges from about 4.5 to about 8, preferably from about 6 to about 7, typically about 6.0+/–0.3, including all ranges and subranges therebetween.

In an embodiment, the invention relates to a water-based gel cosmetic composition comprising:
(a) a viscosity increasing system comprising (I) at least one synthetic non-associative thickening polymer; and (II) at least one synthetic associative thickening polymer;
(b) at least one emulsifier;
(c) at least one film forming polymer;
(d) at least one liquid fatty substance;
(e) water;
(f) optionally a pigment; and
(g) optionally at least one wax;

wherein the compostion has a viscosity of from about 2,000 Pa·s to about 90,000 Pa·s at low shear rate as measured on a TA instrument G2 Rheometer.

Embodiments wherein ratio of non-associative thickener to associative thickener is greater than 1:1

In an embodiment, the invention relates to a water-based gel cosmetic composition comprising:
(a) a viscosity increasing system comprising (I) at least one synthetic non-associative thickening polymer; and (II) at least one synthetic associative thickening polymer;
(b) at least one emulsifier;
(c) of at least one film forming polymer;
(d) at least one liquid fatty substance;
(e) water;
(f) optionally a pigment; and
(g) optionally at least one wax;

wherein the ratio of the at least one synthetic non-associative thickening polymer (a)(I) to the at least one synthetic associative thickening polymer (a)(II) is greater than 1:1; all percentages and ratios being based on the total weight of the composition.

In another embodiment, the invention relates to a water-based gel cosmetic composition comprising:
(a) from about 0.11% to about 4% by weight of a viscosity increasing system comprising (I) from about 0.01% to about 2.0% by weight of at least one synthetic non-associative thickening polymer; and (II) from about 0.1% to about 2.0% by weight of at least one synthetic associative thickening polymer;
(b) from about 0.1% to about 7.5% by weight at least one emulsifier;
(c) from about 0.1% to about 50% by weight of at least one film forming polymer;
(d) from about 0.1% to about 30% by weight of a liquid fatty substance;
(e) from about 5% to about 60% by weight water;
(f) optionally, at least one pigment; and
(g) optionally at least one wax wherein the ratio of the at least one synthetic non-associative thickening polymer (a)(I) to the at least one synthetic associative thickening polymer (a)(II) is greater than 1:1, and wherein the weight percent of each component is based on the total weight of the composition.

In the preceding embodiment, the ratio of the at least one synthetic non-associative thickening polymer (a)(I) to the at least one synthetic associative thickening polymer (a)(II) is preferably from about 1.5:1 to about 3:1, more preferably about 2:1.

In another embodiment the emulsifier comprises at least one gemini surfactant. In a particular embodiment, the gemini surfactant is present in an amount of from about 0.1% to about 1.0% by weight, based on the total weight of the composition.

In another embodiment, the invention relates to a water-based gel cosmetic composition comprising:
- (a) from about 0.11% to about 4% by weight of a viscosity increasing system comprising (I) from about 0.01% to about 2.0% by weight of at least one synthetic non-associative thickening polymer; and (II) from about 0.1% to about 2.0% by weight of at least one associative thickening polymer;
- (b) from about 0.1% to about 1.0% by weight at least one gemini surfactant;
- (c) from about 0.1% to about 5% by weight of at least one film forming polymer selected from a silicone copolymer and from about 0.1% to about 50% by weight of a non-silicone film forming polymer;
- (d) from about 0.1% to about 30% by weight of at least one liquid fatty substance;
- (e) from about 5% to about 60% by weight water;
- (f) optionally, at least one pigment; and
- (g) optionally, at least one wax;

wherein the ratio of the at least one synthetic non-associative thickening polymer (a)(I) to the at least one synthetic associative thickening polymer (a)(II) is greater than 1:1, said composition having a viscosity of from about 2,000 Pa·s to about 90,000 Pa·s at low shear rate and from about 0.1 Pa·s to about 3 Pa·s at high shear rate (Method A); all percentages and ratios being based on the total weight of the composition.

In the immediately foregoing embodiment, if wax is absent, the viscosity tends to be in the lower range, typically between 2,000 Pa·s to about 60,000 s at low shear rate (Method A), while if wax is present, the viscosity is on the higher range, typically from about 8,000 Pa·s to about 90,000 Pa·s at low shear rate (Method A).

In a preferred embodiment of the invention the at least one synthetic non-associative thickening polymer (a)(I) is present in an amount of about 1% by weight, the at least one synthetic associative thickening polymer (a)(II) is present in an amount of about 0.5% by weight, the at least one emulsifier (b) is present in an amount of about 0.75% by weight, the at least one film former (c) is present in an amount from about 2.0% to about 10.5% by weight, the at least one liquid fatty substance (d) is present in an amount of about 11.5% by weight, and water (e) is present in an amount of from about 40% to about 55% by weight, relative to the weight of the final composition.

Embodiments wherein ratio of non-associative thickener to associative thickener is less than or equal to 1:1

In an embodiment, the invention relates to a water-based gel cosmetic composition comprising:
- (a) a viscosity increasing system comprising (I) at least one synthetic non-associative thickening polymer; and (II) at least one synthetic associative thickening polymer;
- (b) at least one emulsifier;
- (c) of at least one film forming polymer;
- (d) at least one liquid fatty substance;
- (e) water;
- (f) optionally a pigment; and
- (g) optionally at least one wax;

wherein the ratio of the at least one synthetic non-associative thickening polymer (a)(I) to the at least one synthetic associative thickening polymer (a)(II) is less than or equal to 1:1; all percentages and ratios being based on the total weight of the composition.

In the above embodiment, the non-associative thickening polymer may be absent (0%).

In another embodiment, the invention relates to a water-based gel cosmetic composition comprising:
- (a) from about 0.11% to about 4% by weight of a viscosity increasing system comprising (I) from about 0.0% to about 2.0% by weight of at least one synthetic non-associative thickening polymer; and (II) from about 0.01% to about 2.0% by weight of at least one synthetic associative thickening polymer;
- (b) from about 0.4% to about 7.5% by weight at least one emulsifier;
- (c) from about 0.1% to about 50% by weight of at least one film forming polymer;
- (d) from about 0.1% to about 30% by weight of a liquid fatty substance;
- (e) from about 5% to about 60% by weight water;
- (f) optionally, at least one pigment; and
- (g) optionally at least one wax wherein the ratio of the at least one synthetic non-associative thickening polymer (a)(I) to the at least one synthetic associative thickening polymer (a)(II) is less than or equal to 1:1; and wherein the weight percent is based on the total weight of the composition.

In the immediately preceding embodiment, the ratio of the at least one synthetic non-associative thickening polymer (a)(I) to the at least on synthetic associative thickening polymer (a)(II) is from about 0:0.5 to about 1:3, more preferably about 1:2.

In another embodiment the emulsifier comprises at least one gemini surfactant. In a particular embodiment, the gemini surfactant is present in an amount of from about 0.1% to about 1.0% by weight, based on the total weight of the composition.

In another embodiment, the invention relates to a water-based gel cosmetic composition comprising:
- (a) from about 0.11% to about 4% by weight of a viscosity increasing system comprising (I) from about 0.1% to about 2.0% by weight of at least one synthetic non-associative thickening polymer; and (II) from about 0.01% to about 2.0% by weight of at least one associative thickening polymer;
- (b) from about 0.1% to about 1.0% by weight at least one gemini surfactant;
- (c) from about 0.1% to about 5% by weight of at least one film forming polymer selected from a silicone copolymer and from about 0.1% to about 50% by weight of a non-silicone film forming polymer;
- (d) from about 0.1% to about 30% by weight of at least one liquid fatty substance;
- (e) from about 5% to about 60% by weight water;
- (f) optionally, at least one pigment; and
- (g) optionally, at least one wax;

wherein the ratio of the at least one synthetic associative thickening polymer (a)(II) to the at least one synthetic non-associative thickening polymer (a)(I) is equal to or greater than 1:1, said composition having a viscosity of from about 3,000 Pa·s to about 90,0000 Pa·s at low shear rate and from about 0.01 Pa·s to about 3 Pa·s at high shear rate (using Method A); all percentages and ratios being based on the total weight of the composition.

In the immediately preceding embodiment, if wax is absent, the viscosity tends to be on the lower range, typically from about 3,000 Pa·s to about 60,000 Pa·s at low shear (Method A), while if wax is present the viscosity is on the higher range, typically from about 9,000 Pa·s to about 90,000 Pa·s In a preferred embodiment the at least one synthetic non-associative thickening polymer (a)(I) is present in an amount of from about 0% to about 1.5% by weight, the at least one synthetic associative thickening polymer (a)(II) is present in an amount of from about 1.0% to about 1.5% by weight, the at least one emulsifier (b) is present in an amount of about 0.75% by weight, the at least one film former (c) is present in an amount from about 3.0% to about 10.5% by weight, the at least one liquid fatty substance (d) is present in an amount of about 11.5% by weight, and water (e) is present in an amount of from about 46% to about 48% by weight, relative to the weight of the final composition.

In another embodiment, the invention relates to a water-based gel cosmetic composition comprising:
  (a) from about 0.1% to about 1.5% by weight of at least one associative thickening polymer;
  (b) from about 0.1% to about 1.0% by weight at least one gemini surfactant;
  (c) from about 0.1% to about 5% by weight of at least one film forming polymer selected from a silicone copolymer and from about 0.1% to about 50% by weight of a non-silicone film forming polymer;
  (d) from about 0.1% to about 30% by weight of at least one liquid fatty substance;
  (e) from about 5% to about 60% by weight water;
  (f) optionally, at least one pigment; and
  (g) optionally, at least one wax;
said composition having a viscosity of from about 4,000 Pa·s to about 90,000 Pa·s at low shear rate and from about 0.01 Pa·s to about 3 Pa·s at high shear rate (Method A); all percentages and ratios being based on the total weight of the composition.

In the above embodiment the associative thickening polymer is typically present in an amount from about 0.1% to about 1.5% by weight, preferably from about 0.2% to about 1.1% by weight, more particularly from about 0.5% to about 1.1% by weight, relative to the weight of the composition.

In the immediately preceding embodiment, if wax is absent, the viscosity tends to be on the lower range, typically from about 4,000 Pa·s to about 60,000 Pa·s at low shear (Method A), while if wax is present the viscosity is on the higher range, typically from about 10,000 Pa·s to about 90,000 Pa·s at low shear rate (Method A).

In any and all of the foregoing embodiments, the composition may further comprises an emollient. When present, the emollient comprises from about 0.1% to about 20% by weight, based on the total weight of the composition.

In another embodiment, the invention relates to a method of improving a property selected from freshness, long wear, comfort, gentle application, color intensity, ease of removal, water and/or oil-resistance, adhesion, malleability and transfer resistance of a gel eyeliner by incorporating in said eyeliner a synthetic non-associative thickening polymer, a synthetic associative thickening polymer, and a film forming polymer.

In another embodiment, the invention relates to a method of making up a keratinous substance, in particular the eyes, with the above described cosmetic composition.

In an embodiment, the synthetic non-associative thickening polymer is ammonium polyacryloyldimethyl taurate ("AMPS", available from Clariant, or from Hoechst under the name Hostacerin AMPS).

In an embodiment, the synthetic associative thickening polymer is ammonium acryloyldimethyltaurate/steareth-8 methacrylate copolymer (available from Clariant).

In another embodiment, the emulsifier is a gemini surfactant selected from disodium ethylene dicocamide PEG-15 disulfate. In a preferred embodiment the gemini surfactant is part of a co-emulsifier system composed of behenyl alcohol (and) glyceryl stearate (and) disodium ethylene dicocamide peg-15 disulfate (and) glyceryl stearate citrate (commercially available from Sasol as CERALUTION® H).

In another embodiment the film-forming polymer is a silicone copolymer. In a particular embodiment the silicone copolymer is divinyldimethicone/dimethicone copolymer (and) C12-13 Pareth-23 (and) Pareth-3 (Dow Corning).

In another embodiment the film-forming polymer is a silicone copolymer in combination with a lipophilic polymer. In a particular embodiment the silicone copolymer is divinyldimethicone/dimethicone copolymer (and) C12-13 Pareth-23 (and) Pareth-3 (Dow Corning) and the lipophilic polymer is C10-C30 alkyl acrylate (Air Products and Chemicals).

In another embodiment the film-forming polymer is a silicone copolymer in combination with a lipophilic polymer and/or a polymethylsiloxane resin. In a particular embodiment the silicone copolymer is divinyldimethicone/dimethicone copolymer (and) C12-13 Pareth-23 (and) Pareth-3 (Dow Corning), the lipophilic polymer is C10-C30 alkyl acrylate (Air Products and Chemicals), and the polymethylsiloxane resin is polymethylsilsesquioxane (Momentive).

In another embodiment, the film forming polymer is selected from a combination of both a silicone copolymer and an acrylate copolymer. In a particular embodiment the silicone film-forming polymer is divinyldimethicone/dimethicone copolymer (and) C12-13 Pareth-23 (and) Pareth-3 (Dow Corning) and the acrylate copolymer is a styrene/acrylates copolymer, acrylates copolymer, styrene/acrylates/ammonium methacrylate copolymer or a mixture thereof.

Thickening Polymers (a)

The synthetic thickening polymers useful in the practice of embodiments of the disclosure include those conventionally used in cosmetics. Representative synthetic thickening polymers include synthetic viscosity increasing polymers and synthetic rheology increasing polymers.

The viscosity increasing system (a) is present in the composition of the invention in an amount of from about 0.11% to about 4.0% by weight, typically from about 0.3% to about 3.0% by weight, more typically from about 0.5% to about 2.15% by weight, more particularly from about 0.8% to about 1.5%, by weight, including all ranges and subranges therebetween, all weights being based on the total weight of the composition.

The gel compositions of the invention may be in the form of an oil in water emulsion.

Synthetic Non-Associative Polymers (a)(I)

These typically high molecular weight polymers increase viscosity when dissolved in the continuous phase by occupying a large volume and immobilizing the continuous phase in the polymer network. See, e.g., Paint & Coating Testing Manual, 14$^{th}$ Edition (J V Koleske Ed., 1995), pp. 268-288; and WO2011/076792. Non-limiting examples of hydrophilic thickeners include modified or unmodified carboxyvinyl polymers, such as the products sold under the name CARBOPOL (CTFA name: carbomer) by Goodrich, homopolymers or copolymers of acrylic or methacrylic acids or the salts thereof and the esters thereof, polyacrylates and polymethacrylates such as the products sold under the names LUBRAJEL and NORGEL by Guardian, or under the name HISPAJEL by Hispano Chimica, and polyacrylic acids of SYNTHALEN K type, polyacrylamides, copolymers of acrylic acid and of acrylamide sold in the form of the sodium salt thereof, such as under the names RETEN® by Hercules, the sodium polymethacrylate such as sold under the name DARVAN 7® by Vanderbilt, and the sodium salts of polyhydroxycarboxylic acids, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (CTFA name: ammonium polyacryldimethyltauramide), crosslinked anionic copolymers of acrylamide and of AMPS, e.g. in the form of a water-in-oil emulsion, such as those sold under the name SEPIGEL™ 305 (CTFA name: Polyacrylamide/C13-14 Isoparaffin/Laureth-7) and under the name SIMULGEL™ 600 (CTFA name: Acrylamide/Sodium acryloyldimethyltaurate copolymer/Isohexadecane/Polysorbate 80) by SEPPIC, polyacrylic acid (available commercially as Carbomers) and acrylates copolymers such as sodium polyacrylate and polyacryloyldimehtyl taurate, and mixtures of these.

Particularly useful synthetic non-associative thickening polymers include sodium acryloyldimethyltaurate/VP crosspolymer, acrylates copolymer, sodium polyacrylate, ammonium acryloyl dimethyltaurate/carboxyethyl acrylate crosspolymer, ammonium polyacryloyldimethyl taurate, ammonium acryloyldimethyltaurate/vinyl formamide copolymer, ammonium polyacryloyldimethyl taurate/ammonium polyacryldimethyltauramide and ammonium acryloyldimethyltaurate/VP copolymer, and mixtures thereof.

In a preferred embodiment, the synthetic non-associative thickening polymer is ammonium polyacryloyldimethyl taurate.

In an embodiment, the synthetic non-associative polymer (a)(I) is present in the composition of the invention in an amount of from about 0.01% to about 2.0% by weight, typically from about 0.1% to about 1.5% by weight, more typically from about 0.5% to about 1.25% by weight, more particularly about 1% by weight, including all ranges and subranges therebetween, all weights being based on the total weight of the composition. In this embodiment, the ratio of (a)(I) to (a)(II) is greater than 1:1.

In another embodiment, the synthetic non-associative polymer (a)(I) is present in the composition of the invention in an amount of from about 0.1% to about 2.0%, typically from about 0.1% to about 1.5%, more typically from about 0.3% to about 1.25%, more particularly about 0.5%, by weight, including all ranges and subranges therebetween, all weights being based on the total weight of the composition. In this embodiment, the ratio of (a)(I) to (a)(II) is equal to or less than 1:1.

In another embodiment, the synthetic non-associative polymer (a)(I) is present in the composition of the invention at 0%, by weight, based on the total weight of the composition. In this embodiment, the at least one synthetic associative thickening polymer (a)(II) is the sole synthetic thickening polymer.

Synthetic Associative Thickening Polymer (a)(II)

Synthetic associative thickening polymers are non-crosslinked or crosslinked polymers that are capable of non-specific hydrophobic associations due to polymers' hydrophobic modification. These hydrophobic associations are chiefly responsible for the increase in viscosity observed with these thickeners. See Paint & Coating Testing Manual, 14$^{th}$ Edition (J V Koleske Ed., 1995), pp. 268-288. In the current invention, the synthetic associative thickening polymers used unexpectedly modified the rheology profile of the resulting composition to afford high pseudoplasticity (that is increased flowability of the compositions at high shear and enhanced product pick-up). Further, incorporation of these polymers resulted in compositions having a larger slope in the corresponding viscosity (Pa·s) versus shear rate (1/s) graph as determined on a TA Instrument G2 Rheometer with a 20 mm 2° cone in continuous or steady state mode. Examples of such polymers are provided in U.S. Pat. No. 7,220,408, which is herein incorporated by reference. See, also, Paint & Coating Testing Manual, 14$^{th}$ Edition (J V Koleske Ed., 1995), pp. 268-288.

The synthetic associative polymers in accordance various exemplary embodiments may be anionic, cationic, nonionic or amphoteric. By way of example, synthetic associative polymers which may be chosen include those comprising at least one hydrophilic unit and at least one fatty-chain allyl ether unit, such as those in which the hydrophilic unit is constituted of an ethylenic unsaturated anionic monomer, such as a vinylcarboxylic acid or an acrylic acid, a methacrylic acid, and mixtures thereof, and in which the fatty-chain allyl ether unit corresponds to the monomer of formula (I) below:

$$CH_2=C(R')CH_2OB_nR \qquad (I)$$

in which R' is chosen from H or $CH_3$, B is chosen from an ethyleneoxy radical, n is zero or is chosen from an integer ranging from 1 to 100, and R is chosen from a hydrocarbon-based radical chosen from alkyl, arylalkyl, aryl, alkylaryl and cycloalkyl radicals containing from 8 to 30 carbon atoms, such as from 10 to 24 carbon atoms, or from 12 to 18 carbon atoms. Exemplary and non-limiting polymers of this type are described and prepared, according to an emulsion polymerization process, in patent EP 0 216 479.

Non-limiting examples of synthetic associative anionic polymers that may also be chosen include anionic polymers comprising at least one hydrophilic unit of olefinic unsaturated carboxylic acid type, and at least one hydrophobic unit exclusively of ($C_{10}$-$C_{30}$)alkyl ester of unsaturated carboxylic acid type. Examples that may be mentioned include, but are not limited to, the anionic polymers described and prepared according to U.S. Pat. Nos. 3,915,921 and 4,509,949, which are herein incorporated by reference.

Cationic associative polymers that may be chosen include, but are not limited to, polyacrylates containing amine side groups.

Exemplary non-ionic associative polymers include copolymers of vinylpyrrolidone and of fatty-chain hydrophobic monomers, for instance Antaron® or Ganex® V216 (vinylpyrrolidone/hexadecene copolymers); Antaron® or Ganex® V220 (vinylpyrrolidone/eicosene copolymers), sold by the company I.S.P., copolymers of $C_1$-$C_6$ alkyl methacrylates or acrylates and of amphiphilic monomers comprising at least one fatty chain, and copolymers of hydrophilic methacrylates or acrylates and of hydrophobic monomers comprising at least one fatty chain, for instance the polyethylene glycol methacrylate/lauryl methacrylate copolymer; polymers with an aminoplast ether skeleton containing at least one fatty chain, such as the Pure Thix® nonionic associative water phase thickeners sold by the company Southern Clay Products, Inc.

Associative polyurethanes may also be chosen in various exemplary and non-limiting embodiments. These are non-ionic block copolymers comprising in the chain both hydrophilic blocks usually of polyoxyethylene nature, and hydrophobic blocks that may be aliphatic sequences alone and/or cycloaliphatic and/or aromatic sequences. Associative polyurethanes comprise at least two hydrocarbon-based lipophilic chains containing from $C_6$ to $C_{30}$ carbon atoms, separated by a hydrophilic block, the hydrocarbon-based chains optionally being pendent chains or chains at the end of a hydrophilic block. For example, it is possible for one or more pendent chains to be provided. In addition, the polymer may comprise a hydrocarbon-based chain at one or both ends of a hydrophilic block. The associative polyurethanes may be arranged in triblock or multiblock form. The hydrophobic blocks may thus be at the each end of the chain (for example, triblock copolymer with a hydrophilic central block) or distributed both at the ends and within the chain (for example, multiblock copolymer). These polymers may also be graft polymers or starburst polymers. For example, the associative polyurethanes may be triblock copolymers in which the hydrophilic block is a polyoxyethylene chain containing from 50 to 1000 oxyethylene groups.

By way of non-limiting example, associative polymers of the polyurethane polyether type that may be used include the polymer $C_{16}$-$OE_{120}$-$C_{16}$ from Servo Delden (under the name SER AD FX1100), which is a molecule containing a urethane function and having a weight-average molecular weight of 1300), OE being an oxyethylene unit, Nuvis® FX 1100 (European and US INCI name "Steareth-100/PEG-136/HMDI Copolymer" sold by the company Elementis Specialties), and also Acrysol RM 184® (sold by the company Rohm and Haas). Further exemplary associative polymers that may be chosen include RHEOLATE® 205 containing a urea function, sold by Rheox, or RHEOLATE® 208 or 204, or RHEOLATE® FX1100 from Elementis. The product DW 1206B from Rohm & Haas containing a $C_{20}$ alkyl chain with a urethane bond, sold at a solids content of 20% in water, may also be used.

In further exemplary embodiments, solutions or dispersions of the above-mentioned polymers, especially in water or in water-alcohol medium, may be chosen. Examples of such polymers include SER AD FX1010, SER AD FX1035 and SER AD 1070 from Servo Delden, and RHEOLATE® 255, RHEOLATE® 278 and RHEOLATE® 244 sold by Rheox. Further examples include the products ACULYN™ 46, DW 1206F and DW 1206J, and also ACRYSOL RM 184 or ACRYSOL 44 from Rohm & Haas, and BORCHIGEL LW 44 from Borchers.

Additional associative thickening polymers include polyacrylic acid/alkyl acrylate copolymers of PEMULEN type; PEG-150/stearyl alcohol/SMDI copolymer such as that sold under the name ACULYN™ 46 by Rohm & Haas; steareth-100/PEG-136/HDI copolymer such as sold under the name RHEOLATE® FX 1100 by Elementis).

Mixtures of the above associative polymers are also contemplated herein as useful in the invention.

As used herein, the term "copolymers" is intended to mean both copolymers obtained from two types of monomers and those obtained from more than two types of monomers, such as, for example, terpolymers obtained from three types of monomers. The chemical structure of the copolymers comprises at least one hydrophilic unit and at least one hydrophobic unit. The expression "hydrophobic unit" or "hydrophobic unit" is understood to mean a radical possessing a saturated or unsaturated and linear or branched hydrocarbon-based chain which comprises at least 8 carbon atoms, for example from 10 to 30 carbon atoms, as a further example from 12 to 30 carbon atoms, and as yet a further example from 18 to 30 carbon atoms.

In certain exemplary and non-limiting embodiments, the associative thickening copolymers are chosen from the copolymers resulting from the polymerization of:
(1) at least one monomer of formula (II):

CH2=CH(R1)COOH (II)

wherein $R_1$ is chosen from H or $CH_3$ or $C_2H_5$, providing acrylic acid, methacrylic acid, or ethacrylic acid monomers, and
(2) at least one monomer of ($C_{10}$-$C_{30}$)alkyl ester of unsaturated carboxylic acid type corresponding to the monomer of formula (III):

CH2=CH(R2)COOR3 (III)

wherein $R_2$ is chosen from H or $CH_3$ or $C_2H_5$, providing acrylate, methacrylate or ethacrylate units, $R_3$ denoting a $C_{10}$-$C_{30}$ alkyl radical, such as a $C_{12}$-$C_{22}$ alkyl radical.

Non-limiting examples of ($C_{10}$-$C_{30}$)alkyl esters of unsaturated carboxylic acids are for example chosen from lauryl acrylate, stearyl acrylate, decyl acrylate, isodecyl acrylate, dodecyl acrylate and the corresponding methacrylates, such as lauryl methacrylate, stearyl methacrylate, decyl methacrylate, isodecyl methacrylate and dodecyl methacrylate, and mixtures thereof.

Additionally, crosslinked thickening polymers may be chosen according to further exemplary embodiments. For example, such polymers may be chosen from polymers resulting from the polymerization of a mixture of monomers comprising:
acrylic acid,
an ester of formula (III) described above, in which $R_2$ is chosen from H or $CH_3$, $R_3$ denoting an alkyl radical having from 12 to 22 carbon atoms, and
a crosslinking agent, which is a well-known copolymerizable polyethylenic unsaturated monomer, such as diallyl phthalate, allyl (meth)acrylate, divinylbenzene, (poly)ethylene glycol dimethacrylate and methylenebisacrylamide.

By way of example, crosslinked thickening polymers comprising about 60% to about 95% by weight of acrylic acid (hydrophilic unit), about 4% to about 40% by weight of $C_{10}$-$C_{30}$ alkyl acrylate (hydrophobic unit), and about 0% to about 6% by weight of crosslinking polymerizable monomer. In yet further embodiments, the crosslinked thickening polymers may comprise about 96% to about 98% by weight of acrylic acid (hydrophilic unit), about 1% to about 4% by weight of $C_{10}$-$C_{30}$ alkyl acrylate (hydrophobic unit), and about 0.1% to 0.6% by weight of crosslinking polymerizable monomer, such as those described above. Examples of such polymers include acrylate/$C_{10}$-$C_{30}$ alkyl acrylate copolymers (INCI name: Acrylates/C10-30 Alkyl Acrylate Crosspolymer), such as the products sold by Lubrizol under the trade names PEMULEN™ TR1, PEMULEN™ TR2, CARBOPOL® 1382 and CARBOPOL® EDT 2020 may be chosen.

In further embodiments, the at least one synthetic associative thickening polymer may be chosen from nonionic homopolymers or copolymers containing ethylenically unsaturated monomers of the ester and/or amide type. For example, the products sold under the names CYANAMER P250 by the company CYTEC (polyacrylamide), methyl methacrylate/ethylene glycol dimethacrylate copolymers (such as PMMA MBX-8C by the company US COSMETICS), butyl methacrylate/methyl methacrylate copolymers (such as ACRYLOID B66 by the company RHOM HMS), and polymethyl methacrylates (BPA 500 by the company KOBO) may be chosen.

Further non-limiting examples of synthetic associative thickening polymers include polyacrylamide (and) C13-14 isoparaffin (and) laureth-7 (such as Sepigel™ 305 from Seppic), acrylates/C10-30 alkyl acrylate crosspolymer (such as Carbopol® Ultrez 20 polymer from Lubrizol), acrylates/C10-30 alkyl acrylate crosspolymer (such as Permulen™

TR-1 from Lubrizol), and polyacrylate crosspolymer-6 (such as Sepimax Zen from Seppic).

In a preferred embodiment, the associative thickening polymers include cross- or co-polymers of polyacryloyl/taurate or polyacryloyl/dimethyltaurate. Non-limiting examples of such polymers include ammonium acryloyldimethyltaurate/steareth-25 methacrylate crosspolymer, ammonium acryloyldimethyltaurate/steareth-8 methacrylate copolymer, ammonium acryloyldimethyltaurate/beheneth-25 methacrylate crossopolymer, and ammonium acryloyldimethyltaurate/laureth-7 methacrylate copolymer, and mixtures thereof.

Additional non-limiting examples of useful associative thickening polymers include acrylates/vinyl neodecanoate crosspolymer, acrylates/steareth-20 methacrylate crosspolymer, and peg-150/stearyl alcohol/SMDI copolymer, and mixtures thereof.

In an embodiment, the associative thickening polymer is also a hydrating agent. A non-limiting example of a synthetic associative thickening polymer that is also a hydrating agent is ammonium acryloyldimethyltaurate/steareth-8 methacrylate copolymer.

The synthetic associative thickening polymer (a)(II) is present in the composition of the invention in an amount of from about 0.1% to about 2.0%, typically from about 0.2% to about 1.5%, more typically from about 0.3% to about 0.9%, more particularly about 0.5%, by weight, including all ranges and subranges therebetween, all weights being based on the total weight of the composition. In this embodiment, the ratio of (a)(I) to (a)(II) is greater than 1:1.

In another embodiment of the invention, the synthetic associative thickening polymer (a)(II) is present in the composition of the invention in an amount of from about 0.1% to about 2.0%, typically from about 0.2% to about 1.5%, more typically from about 0.5% to about 1.5%, more particularly from about 0.5% to about 1.1%, by weight, including all ranges and subranges therebetween, all weights being based on the total weight of the composition. In this embodiment of the invention, the ratio of (a)(I) to (a)(II) is equal to or less than 1:1. In this embodiment (a)(I) can be as low as 0%.

In an embodiment of the invention, the ratio of the at least one synthetic non-associative thickening polymer (a)(I) to the at least one synthetic associative thickening polymer (a)(II) is greater than 1:1, more particularly from about 1.5:1 to about 3:1, even more particularly from about 1.5:1 to about 2.5:1, most preferably about 2:1, by weight, based on the weight percent of each surfactant in the final composition.

In a second embodiment of the invention, the ratio of the at least one synthetic non-associative thickening polymer (a)(I) to the at least on synthetic associative thickening polymer (a)(II) is less than 1:1, more particularly from about 0:1.5 to about 1:3, even more preferably about 1:2.

When anionic thickening polymers are used, they may be neutralized before being included in or as they are added to the compositions of the disclosure. Such anionic thickening polymers may be neutralized by employing traditional neutralizing agents such as alkanolamines, for example, monoethanolamine and diethanolamine; aminomethyl propanol; basic amino acids, for example arginine and lysine; and ammonium compounds and their salts.

Emulsifier (b)

The compositions of the invention contain at least one emulsifier chosen from amphoteric, anionic, cationic and nonionic emulsifiers, used alone or as a mixture. The emulsifiers are appropriately chosen according to the emulsion to be obtained (e.g. W/O or O/W).

Emulsifiers that may be used for the preparation of the W/O emulsions, include sorbitan, glycerol or sugar alkyl esters or ethers; silicone surfactants, for instance dimethicone copolyols, such as the mixture of cyclomethicone and of dimethicone copolyol (sold under the name DC 5225 C by the company Dow Corning), and alkyldimethicone copolyols such as laurylmethicone copolyol (sold under the name Dow Corning 5200 Formulation Aid by the company Dow Corning); cetyldimethicone copolyol (e.g. the product sold under the name Abil EM 90R by the company Evonik), and the mixture of cetyldimethicone copolyol, of polyglyceryl isostearate (4 mol) and of hexyl laurate (e.g. product sold under the name Abil WE O9 by the company Evonik). One or more co-emulsifiers may also be added thereto, which may be chosen for example from the group comprising polyol alkyl esters.

Non-limiting examples of useful polyol alkyl esters include polyethylene glycol esters, for instance PEG-30 dipolyhydroxystearate, such as the product sold under the name Arlacel P135 by the company Croda.

Glycerol and/or sorbitan esters that may especially be mentioned include, for example, polyglyceryl isostearate, such as the product sold under the name Isolan GI 34 by the company Evonik, sorbitan isostearate, such as the product sold under the name Arlacel 987 by the company Croda, sorbitan glyceryl isostearate, such as the product sold under the name Arlacel 986 by the company Croda, and mixtures thereof.

Non-limiting examples of emulsifying polyoxyalkylenated silicone elastomers include those disclosed in U.S. Pat. Nos. 5,236,986, 5,412,004, 5,837,793 and 5,811,487, which are herein incorporated by reference. These silicone elastomers are preferably formulated under the form of a gel in a hydrocarbonated and/or a silicone oil. In those gels, the polyoxyalkylenated silicone elastomer is often under the form of spherical particles.

Examples of polyoxyethylenated silicone elastomers include the following compositions:
a) available from Shin Etsu;
  KSG-16 dimethicone (and) dimethicone/vinyl dimethicone corpsspolymer
  KSG-21 (at 27% in active material) INCI name: Dimethicone/PEG-10 Dimethicone vinyl dimethicone crosspolymer),
  KSG-20 (at 95% in active material) INCI name: PEG-10 Dimethicone Crosspolymer),
  KSG-30, (at 100% in active material) INCI name: Lauryl PEG-15 Dimethicone vinyl dimethicone crosspolymer),
  KSG-31 (at 25% in active material) INCI name: Lauryl PEG-15 Dimethicone vinyl dimethicone crosspolymer),
  KSG-32 or KSG-42 or KSG-320 or KSG-30 (at 25% in active material) INCI name: Lauryl PEG-15 Dimethicone vinyl dimethicone crosspolymer),
  KSG-33: Lauryl PEG-15 (at 20% in active material) Dimethicone vinyl dimethicone crosspolymer),
  KSG-210 (at 25% % in active material) INCI name: Dimethicone/PEG-10/15 crosspolymer),
  KSG-310: lauryl modified polydimethylsiloxane polyoxyethylenated in mineral oil,
  KSG-330 and KSG-340: PEG-15/lauryl dimethicone crosspolymer X-226146 (at 32% % in active material) INCI name: Dimethicone/PEG-10 Dimethicone vinyl dimethicone crosspolymer); and b) available from Dow Corning:
DC9010 (at 9% in active material) and DC9011 (at 11% in active material) INCI name: PEG-12 dimethicone crosspolymer)
DC9040 cyclopentasiloxane (and) dimethicone crosspolymer
DC9041 dimethicone (and) dimethicone crosspolymer; and the like and mixtures thereof.

The above products are typically in the form of oily gel containing the particles of silicone elastomer.

In an embodiment, KSG-210 is used (INCI name: Dimethicone/PEG-10/15 crosspolymer, 25% active silicone elastomer in a silicone oil).

Other silicone elastomers include Polyglycerolated silicone elastomers may also be used as water/oil emulsifiers. Examples of such compounds are provided in WO-A-2004/024798.

Specific examples of polyglycerolated silicone elastomers include the following compositions commercially available from Shin-Etsu: KSG-710 (at 25% in active material, INCI name: dimethicone/polyglycerin-3 crosspolymer); and KSG-820, KSG-830 and KSG-840, all of which are dimethicone/polvaleverin-3 crosspolymer (INCI), but in different diluents, 820 is in isododecane, 830 is in triethyl hexanoin and 840 is in squalene.

For oil-in-water (O/W) emulsions, exemplary emulsifiers that may be used include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate sold, for example, by the company Croda under the name Arlacel 165; oxyalkylenated (oxyethylenated and/or oxypropylenated) fatty alkyl ethers; sugar esters, for instance sucrose stearate; fatty alkyl ethers of sugars, especially alkyl polyglucosides (APG) such as decylglucoside and laurylglucoside sold, for example, by the company Cognis under the respective names Plantaren 2000 and Plantaren 1200, cetostearyl glucoside which optionally can be in a mixture with cetostearyl alcohol, sold, for example, under the name Montanov 68 by the company SEPPIC or sold under the name Tegocare CG90 by the company Evonik or under the name Emulgade KE3302 sold by the company Cognis, and also arachidyl glucoside, for example in the form of a mixture of arachidyl alcohol, behenyl alcohol and arachidyl glucoside, sold under the name Montanov 202 by the company SEPPIC. According to a specific embodiment of the invention, the mixture of the alkyl polyglucoside as defined above with the corresponding fatty alcohol can be in the form of a self-emulsifying composition, for example as disclosed in WO-A-92/06778; the hydrophobically modified inulines as Inuline Lauryl Carbamate as the product sold under the denomination INUTEC SP1 by the Company Beneo-ORAFTI.

According to a specific embodiment of the invention, the emulsifier is a gemini surfactant. Gemini surfactants consist of two conventional surfactant molecules (sometimes also referred to as dimers, which can be identical or different) chemically bonded together by a spacer. The two terminal hydrocarbon tails are hydrophobic. The two polar heads can be cationic, anionic or nonionic and are generally hydrophilic. A variety of spacers can be used. Such surfactants are described for example in the following publications: B S Sekhon, *Gemini (dimeric) Surfactants—The Two-Faced Molecules*, RESONANCE (March 2004), pp. 42-49; Milton J. Rosen, *Gemini Surfactants, Properties of surfactant molecules with two hydrophilic groups and two hydrophobic groups*, Cosmetics & Toiletries magazine, vol. 113 (December 1998), pp. 49-55; and Milton J. Rosen, *Recent Developments in Gemini Surfactants*, Allured's Cosmetics & Toiletries magazine, vol 116, no 7 (July 2001), pages 67-70. These surfactants are known in the art of cosmetics. They are known to have good emulsifying properties for the preparation of emulsions, including oil-in-water (O/W) emulsions. See, e.g., US2005/0724935 (WO 2007/054824, L'Oreal), US2009/0105353 and U.S. Pat. No. 5,863,886, all which are herein incorporated by reference.

According to an embodiment of the invention the emulsifier is an anionic gemini surfactant having the formula (IV)

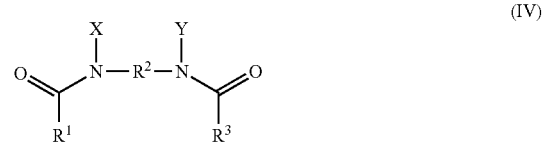

wherein
$R^1$ and $R^3$ are a $C_8$-$C_{25}$ linear alkyl group;
$R^2$ is a $C_2$-$C_8$ alkylene group;
X and Y are independently selected from $(C_2H_4O)n$-RF, where n is 10-15 and
RF is —$SO_3M$, wherein M is an alkaline atom.

A preferred gemini surfactant is the anionic compound disodium ethylene dicocamide -PEG-15 disulfate (INCI name, also known as sodium dicocoyl ethylene diamine PEG-15 sulfate (non INCI name)) having the formula:

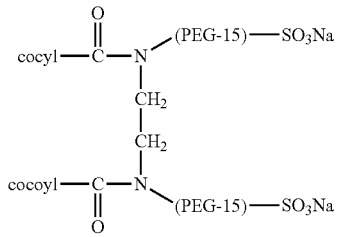

The gemini surfactant may be used, for example, as a mixture with other surfactants or co-emulsifiers, such as for example in the form of products sold by the company Sasol under the trade name Ceralution®. The following are particularly preferred gemini surfactant- and co-emulsifier-containing compositions:

Ceralution® H: behenyl alcohol, glyceryl stearate, glyceryl stearate citrate and sodium dicocoylethylenediamine PEG-15 sulfate;

Ceralution® F: sodium lauroyl lactylate and sodium dicocoylethylenediamine PEG-15 sulfate;

Ceralution® C: aqua, capric/caprylic triglyceride, glycerin, ceteareth-25, sodium dicocoylethylenediamine PEG-15 sulfate, sodium lauroyl lactylate, behenyl alcohol, glyceryl stearate, glyceryl stearate citrate, gum arabic, xanthan gum, phenoxyethanol, methyl paraben, ethyl paraben, butyl paraben isobutyl paraben (INCI names).

In a preferred embodiment the gemini surfactant is the mixture of behenyl Alcohol, Glyceryl Stearate, Glyceryl Stearate Citrate and Sodium Dicocoyl ethylenediamine PEG-15 Sulfate (Ceralution® H).

In the Ceralution®-type of surfactant system, the gemini surfactant represents from about 3% to about 50% of the weight of these mixtures.

Other emulsifiers or co-emulsifiers that may also be used include fatty esters of citric acid; long chain alcohols, polyols and polyol derivatives, such as for example cetyl alcohol and stearyalcohol; isophthalic acid polymers or sulfo isophthalic acid polymers, and specifically copolymers of phthalate/sulfo isophthalate/glycol, such as for example diethylene glycol/phthalate/isophthalate/1,4-cyclohexane-dimethanol copolymer (INCI name: Polyester-5sol), available from Eastman Chemical under the tradename Eastman AQ® polymer (AQ35S, AQ38S, AQ55S, AQ48 Ultra).

Polyurethane polyether polymers may also be used as emulsifiers. Examples of such polymers include Elfacos® T210® (C12-C14 alkyl chain) and Elfacos® T212® (C18 alkyl chain) sold by Akzo.

In an embodiment the emulsifier is selected from long chain fatty alcohols, fatty esters of polyols, fatty acids, and mixtures thereof.

The emulsifier is present in the composition of the invention in an amount of from about 0.2% to about 7.5%, preferably from about 2% to about 6%, most preferably about 5%, by weight, including all ranges and subranges therebetween, all weights being based on the total weight of the composition.

Film-Forming Polymer (c)

As used herein, the terms "film-forming polymer," "film former," "film-forming agent" and variations thereof mean a polymer capable of, by itself or in the presence of an auxiliary film-forming polymer, forming a continuous film that adheres to a support and especially to keratin materials, for instance the eyes.

The film-forming polymers that may be used in the cosmetic compositions disclosed herein include, for example, acrylate copolymers, styrene/acrylate copolymers, acrylaminde/acrylate copolymers, polyurethanes, silicone resins and block silicone copolymer particles, and other resins, and derivatives thereof and mixtures thereof.

In accordance with various exemplary embodiments, acrylate copolymers may be chosen from copolymers comprising two or more monomers chosen from acrylic acid, methacrylic acid, and their simple esters, for example, lower alkyl esters such as methyl, ethyl, and ethylhexyl esters.

By way of non-limiting example only, acrylate copolymers may be chosen from styrene acrylates/copolymers, ammonium acrylates copolymers, ethyl acrylates copolymers, acrylates/ethylhexylacrylate copolymers, acrylates/octylacrylates copolymers, alkyl (meth)acrylates copolymers, acrylates/$C_{12}$-$C_{22}$ alkylmethacrylate copolymers, ethylacrylate/methacrylic acid copolymer, and t-butyl acrylate/ethyl acrylate/methacrylic acid copolymer. Exemplary commercial acrylate copolymers include, but are not limited to, ALLIANZ™ OPT sold by Ashland Specialty Ingredients; COVACRYL A15 and COVACRYL E14 sold by Sensient Cosmetic Technologies LCW; DAITOSOL 4000 SJT, DAITOSOL 5000 AD, DAITOSOL 5000 SJ, KOBOGUARD® 50A, and KOBOGUARD® 50N sold by Kobo Products, Inc.; DERMACRYL® AQF, YODOSOL 32A707, YODOSOL GH15, YODOSOL GH32, YODOSOL GH33, YODOSOL GH34, YODOSOL GH35, YODOSOL GH800, and YODOSOL GH810 sold by AkzoNobel; LUVIFLEX® SOFT, LUVIMER® 36D, and LUVIMER® 100P sold by BASF; and NEOCRYL XK-90 sold by Neoresins, Inc.

The film forming polymer may also be chosen from polyacrylates such as polyacrylate-21, and polyacrylate-15, and acrylates copolymer.

In another embodiment the at least one film forming polymer can be selected from a lipophilic polymer, such as for example, poly $C_{10-30}$ alkylacrylates (available as Intelimer® IPA 13-1 from Air Products).

Latex Film Formers

The film-forming polymer may also be chosen from latex film forming polymers such as polyacrylate latex, polyurethrane latex, and their copolymers.

Suitable examples of latex polymers for use in the present invention are ethylhexyl acrylate/hema copolymer (and) acrylates/diethylaminoethyl methacrylate/ethylhexyl acrylate copolymer (Syntran® PC 5775), styrene/acrylates/ammonium methacrylate copolymer (Syntran® 5760, Syntran® 5009, Syntran® PC5620), polyacrylate-21 (and) acrylates/dimethylaminoethyl methacrylate copolymer (Syntran® PC5100, Syntran® PC5776, Eudragit E 100, Jurymer ET-410C), styrene/acrylates/ammonium methacrylate copolymer (Syntran® 5009 CG), olefin/acrylate grafted polymer (and) sodium laureth sulfate (and C12-15 SECpareth 15 (Syntran® EX108), acrylates copolymer (Aculyn® 33A Polymer, Avalure® Ace 210/120/315 Acrylic Copolymer, Carbopol Aqua SF-1® Polymer, Daitosol® 500 AD, Coatex® Co 633, Eliclear® 380/700/4U, Eudragit® L 100, Joncryl® 85, Luviflex® Soft), acrylates/ethylhexyl acrylate copolymer (Daitosol® 5000SJ, Daitosol® 4000SJT, MJA PS34-21, SDP-001). The Syntran® polymers are commercially available from the supplier Interpolymer Corp.

Suitable examples of latex polymers are polyurethane-35, polyurethane-35, and polyurethane-35.

In an embodiment, the latex polymer is an acrylate latex polymer, in particular styrene/acrylate copolymers. Non-limiting examples of commercially available styrene/acrylate copolymers include, but are not limited to, DAITOSOL 5000 STY sold by Kobo Products, Inc.; JONCRYL® 77 sold by BASF; NEOCRYL BT-62 sold by Neoresins, Inc.; RHOPLEX™ P-376 and UCAR™ DL 432S sold by Dow Chemical Company; and YODOSOL GH41 and YODOSOL GH840 sold by AkzoNobel.

In further exemplary embodiments, acrylamide/acrylate copolymers may be chosen from acrylic acid/ethyl acrylate/t-butyl acrylamide copolymer, acrylates/octylacrylamide copolymer, and octylacrylamide/acrylates/methacrylates copolymer. Exemplary commercial acrylamide/acrylate copolymers include, but are not limited to AMPHOMER® LV-71 and DERMACRYL® 79 sold by AkzoNobel and ULTRAHOLD® STRONG sold by BASF.

According to additional exemplary embodiments, polyurethanes may be chosen from polyurethane-32, polyurethane-34, and polyurethane-35. Exemplary commercial polyurethanes include, but are not limited to, products sold by Bayer under the trade name BAYCUSAN®, such as BAYCUSAN® C1000, BAYCUSAN® C1001, BAYCUSAN® C1003, and BAYCUSAN® C1004.

In at least one exemplary embodiment, the latex film former may be chosen from blends comprising a combination of latex film formers, including, for example, a blend of any of the above-mentioned film formers. By way of non-limiting example, a latex film forming blend useful according to the disclosure may comprise (1) at least one random styrene acrylate copolymer or derivatives thereof, and at least one acrylate copolymer or derivatives thereof, or (2) at least two random styrene acrylate copolymers or derivatives thereof.

In an embodiment the film former is selected from styrene/acrylates/ammonium methacrylate copolymers sold by Interpolymer Corporation, in particular SYNTRAN® 5760 (styrene/acrylates/ammonium methacrylate copolymer (and) sodium laureth sulfate (and) caprylyl glycol); SYNTRAN® 5775 (acrylates/ethylhexyl acrylate/hema copolymer (and) acrylates/diethylaminoethylmethacrylate/ehtylhexyl acrylate copolymer (and) isodeceth-6 (and) caprylyl glycol (and) sodium laureth sulfate); SYNTRAN® Ex 108 (olefin/acrylate grafted polymer (and) sodium laureth sulfate (and) C12-15 SEC-pareth 15); and SYNTRAN® 108 GC (olefin/acrylic grafted emulsion).

According to at least certain exemplary embodiments of the disclosure, the at least one latex film former may be chosen from those having a glass transition temperature (Tg) ranging from about −15° C. to about 90° C., such as from about 0° C. to about 50° C.

Silicone Resins

In accordance with other exemplary embodiments, silicone resins and copolymers may also be used as a film forming agent. In a particular embodiment, the at least one firm forming polymer is a silicone copolymer.

Film-forming silicone resins and copolymers are described, for example, in U.S. Pat. No. 7,790,148 (L'Oreal), U.S. Pat. No. 7,094,842 (L'Oreal), US2011/0189,117 (L'Oreal), US2010/0297050 (L'Oreal), US 2007/0093619 and 2006/0013791, 2005/0201961, all of which are herein incorporated by reference.

Exemplary film forming silicone resins are crosslinked polyorganosiloxane polymers. The nomenclature of silicone resins is known under the name "MDTQ", the resin being described as a function of the various monomeric siloxane units it includes, each of the letters "MDTQ" characterizing one type of unit. Examples of commercially available polymethylsilsesquioxane resins that may be mentioned are those that are sold by the supplier Wacker under the reference Resin MK such as Belsil® PMS MK, and by the supplier SHIN-ETSU under the references KR-220L.

Examples of commercially available polypropylsilsesquioxane resins useful in the invention include those sold under the reference DC®670 by the supplier Dow Corning, and Silform® Flexible Resin from the supplier Momentive.

Examples of a polyphenylsilsesquioxane resins useful in the invention include those available from Wacher.

Siloxysilicate resins that may be used include trimethylsiloxysilicate resins (TMS®) such as those sold under the reference SR1000 by the supplier Momentive Performance Materials or under the reference TMS® 803 by the supplier Wacker. Trimethylsiloxysilicate resins are also available in a solvent such as cyclomethicone, sold under the name "KF-7312J" by the supplier Shin-Etsu, or "DC® 749", "DC® 593" by the supplier Dow Corning.

Pressure-sensitive adhesive silicone copolymers are also herein contemplated. Such copolymers are available, for example from Dow Corning under the reference BIO-PSA and described in U.S. Pat. No. 5,162,410.

Silicone copolymers derived from the reaction of a silicone resin such as those described above and of a diorganosiloxane such as that described in the document WO 2004/073626 are also contemplated.

Block Silicone Copolymer Particles

Block silicone copolymer particles are also useful in preparing films according to the invention. These silicone compounds are described in U.S. Pat. No. 7,094,842. The silicone copolymer constituting the globules or particles in dispersion in the aqueous phase is a substantially linear block copolymer, that is to say a non-crosslinked copolymer, obtained by chain extension and not by crosslinking.

The aqueous dispersion of particles of block copolymer is a silicone-in-water emulsion (Sil/W) wherein the oily globules are constituted from a silicone of high viscosity, so that these globules seem to form as "soft particles".

The composition may comprise dispersions of one or more types of substantially linear block silicone copolymer. These block silicone copolymers are present in the composition of the invention in concentrations, as active material, which may vary widely depending on the other ingredients of the composition and the desired aim. The concentration, as active material (A.M.), of block silicone copolymer preferably ranges from 0.01 to 15% by weight, even better from 0.1 to 10% by weight, and better still from 0.5 to 5% by weight, including all ranges and subranges therebetween, relative to the total weight of the composition.

The size of the block silicone copolymer particles vary. Preferably, in the present invention, the silicone copolymer particles generally have a number-average size of less than or equal to 2 microns, and preferably of less than or equal to 1 micron.

The aqueous dispersions of substantially linear block silicone copolymer particles used according to the invention may be chosen in particular from those described in the document EP-A-874017, whose teaching is incorporated into the present by reference. According to this document, it is possible in particular to obtain the silicone copolymers constituting these particles by chain extension reaction, in the presence of a catalyst, from at least:

(a) one polysiloxane (i) having at least one reactive group and preferably one or two reactive groups per molecule; and (b) one organosilicone compound (ii) which reacts with the polysiloxane (i) by chain extension reaction.

In a particular embodiment, the polysiloxane (i) is chosen from a compound of formula (V):

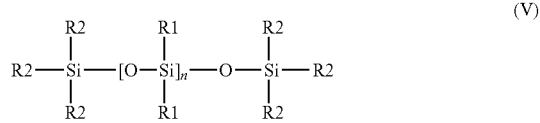

wherein $R_1$ and $R_2$, independently of each other, represent a hydrocarbon group having from 1 to 20 carbon atoms and preferably from 1 to 10 carbon atoms, such as methyl, ethyl, propyl or butyl, or an aryl group such as phenyl, or a reactive group, n is an integer greater than 1, provided that there is on average between one and two reactive groups per polymer.

As used above in defining formula (V), the expression "reactive group" is understood to mean any group capable of reacting with the organosilicone compound (ii) to form a block copolymer. As reactive groups, there may be mentioned hydrogen; aliphatically unsaturated groups and in particular vinyl, allyl or hexanyl groups; the hydroxyl group; alkoxy groups such as methoxy, ethoxy or propoxy; alkoxyalkoxy groups; the acetoxy group; amino groups, and mixtures thereof. Preferably, more than 90%, most preferably more than 98% of reactive groups are at the chain end, that is to say that the radicals $R_2$ generally constitute more than 90% and even 98% of the reactive groups.

Preferably, n is such that the polysiloxanes have a viscosity ranging from about 1 to $1\times10^6$ mm$^2$/sec at 25° C. n may be for example an integer ranging from about 5 to 30, preferably from 10 to 30 and better from 15 to 25.

The polysiloxanes of formula (V) are substantially linear polymers, that is to say containing few branches, and generally less than 2 mol % of the siloxane units. Moreover, the groups $R_1$ and $R_2$ may be optionally substituted with amino groups, epoxy groups, groups containing sulphur, silicon or oxygen.

Preferably, at least 80% of the groups $R_1$ are alkyl groups and even better methyl groups.

Preferably, the reactive group $R_2$ at the chain end is an aliphatically unsaturated group and in particular a vinyl group.

As polysiloxanes (i), there may be mentioned in particular dimethylvinylsiloxypolydimethylsiloxane, a compound of formula (V) in which the radicals $R_1$ are methyl radicals, and, at the chain end, the radical $R_2$ is a vinyl radical while the other two radicals $R_2$ are methyl radicals.

The organosilicone compound (ii) may be chosen from the polysiloxanes of formula (V) or compounds acting as chain extension agent. If it is a compound of formula (V), the polysiloxane (i) will contain a first reactive group and the organosilicone compound (ii) will contain a second reactive group which will react with the first. If it is a chain extension agent, it may be a silane, a siloxane (disiloxane or trisiloxane) or a silazane. Preferably, the organosilicone compound (ii) is a liquid organohydrogenpolysiloxane of formula (VI):

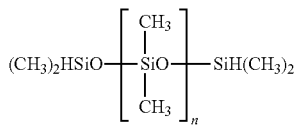

VI wherein is an integer greater than 1 and preferably greater than 10, and for example ranging from 5 to 30, preferably from 10 to 30, and better from 15 to 25. According to a particular embodiment of the invention, "n" is equal to 20.

The block silicone copolymers used according to the invention are advantageously free from oxyalkylenated groups, especially free from oxyethylenated and/or oxypropylenated groups.

The catalyst of the reaction between the polysiloxane and the organosilicone compound may be chosen from metals and in particular from platinum, rhodium, tin, titanium, copper and lead. It is preferably platinum or rhodium.

The dispersion of silicone copolymer particles used according to the invention may in particular be obtained, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture so that the chain extension reaction only starts in the dispersion.

As emulsifiers which may be used in the method of preparation described above for obtaining the aqueous dispersion of particles, there may be mentioned non-ionic or ionic (anionic, cationic or amphoteric) emulsifiers. They are preferably non-ionic emulsifiers which may be chosen from polyalkylene glycol ethers of a fatty alcohol, containing from 8 to 30 carbon atoms and preferably from 10 to 22 carbon atoms; polyoxyalkylenated and in particular polyoxyethylenated alkyl esters of sorbitan, where the alkyl radical contains from 8 to 30 carbon atoms and preferably from 10 to 22 carbon atoms; polyoxyalkylenated and in particular polyoxyethylenated alkyl esters, where the alkyl radical contains from 8 to 30 carbon atoms and preferably from 10 to 22 carbon atoms; polyethylene glycols; polypropylene glycols; diethylene glycols; and mixtures thereof. The quantity of emulsifier(s) is generally from 1 to 30% by weight relative to the total weight of the reaction mixture.

The emulsifier used to obtain the aqueous dispersion of particles is preferably chosen from polyethylene glycol ethers of fatty alcohols and mixtures thereof, in particular polyethylene glycol ethers of alcohols containing 12 or 13 carbon atoms or from 2 to 100 oxyethylenated units and preferably from 3 to 50 oxyethylenated units, and mixtures thereof. There may be mentioned, for example, $C_{12}$-$C_{13}$ Pareth-3, $C_{12}$-$C_{13}$ Pareth-23 and mixtures thereof.

According to a particular embodiment of the invention, the dispersion of particles of silicone copolymer is obtained from dimethylvinylsiloxypolydimethylsiloxane (or divinyldimethicone) as compound (i), and from the compound of formula (II) with preferably n=20, as compound (ii), preferably in the presence of a platinum-type catalyst, and the dispersion of particles is preferably obtained in the presence of $C_{12}$-$C_{13}$ Pareth-3 and $C_{12}$-$C_{13}$ Pareth-23 as emulsifiers.

A non-limiting example of dispersion of particles of silicone copolymer is divinyldimethicone/dimethicone copolymer (and) C12-13 pareth-23 (and) C12-13 pareth-3 (INCI name, commercially available as HMW 2220 from Dow Corning; containing about 60% by weight of divinyldimethicone/dimethicone copolymer).

Particular Embodiments of Film-Forming Polymers

In particular exemplary embodiments, the film forming-polymer is a silicone film forming polymer selected from siloxysilicate resins, in particular trimethylsiloxysilicate resin.

In another particular embodiment, the at least one silicone film forming polymer is selected from polypropylsilsesquioxane resin, acrylates/dimethicone copolymers, cyclohexasiloxane, cyclopentasiloxane, cetyl PEG/PPG-10/1 dimethicone, Nylon-611/Dimethicone copolymer, polyglycerin modified branched silicone crosspolymers, divinyldimethicone/dimethicone copolymers, and mixtures thereof.

In another embodiment the film former is selected from an acrylates copolymer, such as acrylates/ethylhexyl acrylate copolymer, commercially available from KOBO under the name DIATOSOL®.

another particular embodiment the film former is selected from a styrene/acrylates copolymer.

In another embodiment the film former is selected from both an acrylate copolymer, such as styrene/acrylates copolymer, and a silicone copolymer, such as divinyldimethicone/dimethicone copolymer.

In another embodiment the film forming polymer may also be selected from a natural resin/polymer, such as shellac and its derivatives.

The at least one film-former (c) is present in the composition of the invention in an amount of from about 0.1% to about 50%, preferably from about 0.2% to about 20%, more preferably from about 0.5% to about 10%, particularly from about 1% to about 4%, most preferably about 3%, including all ranges and subranges therebetween, by weight, all weights being based on the total weight of the composition.

In an embodiment wherein the film former is acrylate-based, the amount of film former in the composition is from about 0.1% to about 50%, typically from about 1% to about 40%, more typically from about 1% to about 30%, including all ranges and subranges therebetween, by weight, all weights being based on the total weight of the composition.

In another embodiment wherein the film former is silicone-based, the amount of film former in the composition is from about 0.1% to about 20%, typically from about 0.5% to about 15%, including all ranges and subranges therebetween, by weight, all weights being based on the total weight of the composition. When the film former is a silicone resin, the amount of the silicon resin in the composition is typically from about 2% to about 15%, most typically from about 5% to about 10%, including all ranges and subranges therebetween, by weight, all weights being based on the total weight of the composition. When the film former is a silicone block copolymer, it is present in the composition in an amount from about 0.1% to about 5%, most typically about 3%, including all ranges and subranges therebetween, by weight, all weights being based on the total weight of the composition.

In another embodiment wherein the film former includes both an acrylate-based polymer and a silicone-based block polymer, the silicone-based block copolymer is present in an amount of from about 0.1% to about 5%, typically about 3%, and the acrylate-based polymer is present in an amount of from about 0.1% to about 50%, more typically about 1% to about 30%, including all ranges and subranges therebetween, by weight, all weights being based on the total weight of the composition.

In another embodiment the film former includes an acrylate-based polymer, a silicone resin copolymer and a silicone block copolymer. In this embodiment, the silicone resin copolymer is present in an amount of from about 0.1% to about 15%, more typically from about 1% to about 15%, the silicone block copolymer is present in an amount of from about 1% to about 5%, typically about 3%, and the acrylate-based polymer is present in an amount of from about 1% to about 20%, more typically about 5% to about 15%, including all ranges and subranges therebetween, by weight, all weights being based on the total weight of the composition.

In another embodiment the film former includes a silicone resin and a silicone block copolymer. In this embodiment, the amount of the silicone resin in the composition is from about 0.1% to about 20%, more typically from about 1% to about 15%, and the silicone block copolymer is present in an amount of from about 1% to about 5%, typically about 3%, including all ranges and subranges therebetween, by weight, all weights being based on the total weight of the composition.

In another embodiment the film former includes an acrylates-based polymer and a silicone resin. In this embodiment, the silicone resin copolymer is present in an amount of from about 0.1% to about 20%, more typically from about 1% to about 15%, and the acrylate-based polymer is present in an amount of from about 0.1% to about 50%, more typically about 1% to about 30%, including all ranges and subranges therebetween, by weight, all weights being based on the total weight of the composition.

Liquid Fatty Substance (d)

The compositions according to the invention contain a liquid fatty substance which may be selected, for example, from organic solvents and volatile and/or non-volatile oils, and mixtures thereof. These oils include low viscosity oils (having a viscosity from about 5 to about 10 centipoise) and high viscosity oils (having a viscosity of from about 100 to about 10,000 centipoise), and mixtures thereof. These fatty substances are liquid at room temperature.

Representative suitable solvents include non-polar volatile hydrocarbon-based oils include isodecane and isododecane, and for example, the oils sold under the trade names Isopar™ or Permythyl®. Preferably, the volatile oils have a flash point of at least 40° C.

Other exemplary organic solvents are non-volatile solvents which include polyalphaolefins such as hydrogenated polydecene, hydrogenated C6-14 olefin polymers and polydecene.

Natural oils may also be used so long as they are physiologically acceptable. Such oils include hydrocarbon-based plant oils with a high triglyceride content such as sweet almond oil, avocado oil, olive oil, candlenut oil, vitamin E oil, and the like.

Volatile and non-volatile silicone oils, may also be used. Such oils are described, for example in US 2011/0293550, which to the extent required, is herein incorporated by reference. Suitable silicone oils include, for instance, volatile or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane; polydimethyl-siloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes; and dimethicone fluids having viscosity values of equal to or greater than 300 cPs; and mixtures thereof.

The fatty substance may also be selected from non-silicone oils such as hydrogenated polyisobutene; and fatty esters such as isostearyl hydroxy sterate, glyceryl ethylhexanoate/stearate/adipate, pentaerythrityl tetraethylhexanoate, isononyl isononanoate, and isopropyl lauroyl sarcosinate; and mixtures thereof.

In a particular embodiment the liquid fatty substance is selected from dimethicone, dimethicone (and) dimethiconol, phenyl trimethicone, glyceryl ethylhexanoate/stearate/adipate, isostearyl hydroxyl sterate, and mixtures thereof.

The liquid fatty substance (d) is present in the composition of the invention in an amount of from about 0.1% to about 30%, preferably from about 0.5% to about 20%, more particularly from about 1% to about 17%, most particularly about 2% to about 15%, by weight, including all ranges and subranges therebetween, all weights being based on the total weight of the composition.

Water (e)

The compositions for the invention also comprise water in an amount ranging from about 5% to about 60%, preferably from about 10% to about 55%, most typically from about 40% about 50%, including all ranges and subranges therebetween, by weight, relative to the total weight of the compositions.

The compositions of the invention may include additional solvents. In particular, the aqueous phase may include at least one organic solvent that is water-miscible. Non-limiting examples of suitable organic solvents include $C_{1-4}$ alkanols, such a sethanol and isopropanol; glycerol; glycols and glycol ethers such as 2-butoxyethanol, propylene glycol, butylene glycol, monomethyl ether of propylene glycol, monethyl ether and monomethyl ether of diethylene glycol, aromatic alcohols such as benzyl alcohol and phenoxyethanol; analogous products and mixtures of the foregoing products.

Other solvents include caprylic/capric acid triglycerides (such as those sold under the trade name Miglyol®.

In addition to water, the compositions of the invention may comprise a solvent in an amount ranging from about 0.1% to about 10%, preferably from about 3% to about 6%, including all ranges and subranges therebetween, by weight, relative to the total weight of the compositions.

Pigments (f)(Optional)

The cosmetic composition of the invention may optionally include at least one pigment or dyestuff. Suitable pigments/dyes include, but are not limited to, pulverulent dyestuffs, liposoluble dyes, water-soluble dyes, and pearling agents.

The pulverulent dyestuffs may, for instance, be chosen from pigments and nacres. Useful pigments include titanium dioxide, zirconium oxide, zinc oxide, cerium oxide, iron oxide, chromium oxide, manganese violet, ultramarine blue, chromium hydrate, and ferric blue. Non-limiting examples of organic pigments include carbon black, pigments of D&C type, and lakes based on cochineal carmine, barium, strontium, calcium, and aluminum.

The nacres which may be used include, for example, mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

Representative liposoluble dyes which may be used according to the present invention include Sudan Red, DC® Red 17, DC® Green 6, beta-carotene, soybean oil, Sudan Brown, DC® Yellow 11, DC® Violet 2, DC® Orange 5, annatto, and quinolone yellow.

In an embodiment the pigment is iron oxides.

The at least one pigment/dyestuff may be present in the cosmetic composition in an amount ranging from about 5% to about 30%, more particularly from about 10% to about 25%, particularly about 20%, including all ranges and subranges therebetween, by weight, relative to the total weight of the compositions.

Wax (g) (Optional)

While the compositions of the invention optionally may include wax, they also may be devoid of waxes (e.g. having less than about 5% wax, preferably 0%).

For the purposes of the present invention, the term "wax" is understood to mean a lipophilic compound, which is solid at room temperature (25° C.), with a reversible solid/liquid change of state, which has a melting point of greater than or equal to 30° C., which may range up to 120° C. The melting point of the wax may be measured using a differential scanning calorimeter (DSC), for example the calorimeter sold under the name DSC 30 by Mettler. For waxes that are derived from petroleum, such as microcrystalline wax, the melting point may be measured according to the drop ASTM method, D-127.

The waxes may be hydrocarbon-based waxes, fluoro waxes and/or silicone waxes and may be of plant, mineral, animal and/or synthetic origin. In particular, the waxes have a melting point of greater than 25° C. and better still greater than 45° C.

Hydrocarbon-based waxes, for instance beeswax, lanolin wax or Chinese insect wax; rice wax, carnauba wax, candelilla wax, ouricury wax, esparto grass wax, cork fibre wax, sugarcane wax, Japan wax and sumach wax; montan wax, microcrystalline waxes, paraffins and ozokerite, polyethylene waxes, the waxes obtained by Fisher-Tropsch synthesis and waxy copolymers, and also esters thereof, may be included in the compositions of the invention.

Also useful are waxes obtained by catalytic hydrogenation of animal or plant oils containing linear or branched C8-C32 fatty chains. Among these waxes, mention may especially be made of hydrogenated jojoba oil, isomerized jojoba oil such as the trans-isomerized partially hydrogenated jojoba oil manufactured or sold by Desert Whale under the commercial reference ISO-JOJOBA-50®, hydrogenated sunflower oil, hydrogenated castor oil, hydrogenated coconut oil, hydrogenated lanolin oil, bis(1,1,1-trimethylolpropane) tetrastearate sold under the name HEST 2T-4S® by Heterene and bis(1,1,1-trimethylol-propane) tetrabehenate sold under the name HEST 2T-4B® by Heterene.

The wax obtained by hydrogenation of olive oil esterified with stearyl alcohol, sold under the name PHYTOWAX® OLIVE 18L57 and the waxes obtained by hydrogenation of castor oil esterified with cetyl alcohol sold under the names PHYTOWAX® RICIN 16L64 and 22L73 by Sophim may also be used. Such waxes are described in patent application FR-A-2 792 190, which is herein incorporated by reference.

The at least one wax that may be present invention may also be a polar wax. The expression "polar wax" is understood to mean waxes comprising in their chemical structure, in addition to carbon and hydrogen atoms, at least one highly electronegative heteroatom, such as O, N or P.

The wax may also be chosen from silicone waxes and siloxane resin waxes (also known as silsesquioxane resin waxes). Useful silicone waxes include alkyl or alkoxy dimeticones containing from 16 to 45 carbon atoms, and fluoro waxes.

A suitable example of a silsesquioxane resin wax is a propylsilsesquioxane wax substituted with alkyl units having from 9-40 carbon atoms, preferably, at least 30 carbon atoms. Propylsilsesquioxane waxes, are generally described in patent publication WO2005/100444.

If present, the wax of the present invention is chosen from carnauba wax, candelilla wax, natural (or bleached) beeswax, synthetic beeswax, paraffin wax, silicone waxes, and silsesquioxane resin waxes. As synthetic beeswax, mention may be made of the wax sold under the name CYCLO-CHEM® 326 A by Evonik Goldschmidt (INCI name: Synthetic Beeswax).

Wax can be present in the composition of the invention in an amount of from about 0.1% to about 15%, preferably from about 5% to about 10%, most typically about 5%, including all ranges and subranges therebetween, by weight, all weights being based on the total weight of the composition.

Emollients (Optional)

The compositions of the invention include one or more emollient and/or humectants and/or moisturizers (herein "emollients"). These compounds hydrate the keratinous substrate, including the eye lids, and also provide a "wet" texture and shiny look. Emollients are known to skilled artisan. See, e.g. *International Cosmetic Ingredient Dictionary and Handbook Vol. 4* (9th ed. 2002), more particularly the emollients disclosed on pages 2930-2936. The disclosure of the *International Cosmetic Ingredient Dictionary and Handbook Vol. 4*, pages 2930-2936, is hereby incorporated by reference.

Without limitation, the emollients that may be used in the compositions of the invention include, for example: glycerin; glycerol; propylene glycol; butylene glycol; carnauba wax; beeswax; candelilla; ozokerite; paraffin; rice bran wax; microcrystalline wax; polyethylene wax; mineral oil; almond oil; castor oil; sesame oil; hydrogenated polyisobutene; butylene glycol dicaprylte dicaprate (commercially available from Sasol as Myglyol®); and mixtures thereof.

In a particular embodiment the emollient is butylene glycol.

The emollient is present in the composition of the invention in an amount of from about 0.1% to about 20%, preferably from about 1% to about 15%, more particularly from about 3% to about 10%, by weight, including all ranges and subranges therebetween, all weights being based on the total weight of the composition.

Fillers (Optional)

The cosmetic composition disclosed herein may also comprise at least one filler commonly used in the art in cosmetic compositions. The fillers may be lamellar or non-lamellar, inorganic or organic particles. Representative, non-limiting examples of these ingredients include mica, silica, kaolin, iron oxides, titanium dioxide, polyamide powders, polyamide powders, for instance Nylon® (Orgasol from Atochem), poly-alanine powders, polyethylene powders, tetrafluoroethylene polymer powders, for instance polytetrafluoroethylene(Teflon®), lauroyllysine, starch, boron nitride, hollow polymer microspheres such as those of polyvinylidene chloride/acrylonitrile, for instance Expancel® (Nobel Industrie), acrylic powders such as Polytrap® (Dow Corning), polymethyl methacrylate particles and silicone resin microbeads (for example, Tospearls® from Toshiba), methylsilanol/silicate crosspolymer, precipitated calcium carbonate, magnesium carbonate, magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms, preferably from 12 to 18 carbon atoms, for example, zinc stearate, magnesium stearate, lithium stearate, zinc laurate, or magnesium myristate.

The fillers, if present, are present in amounts generally ranging from about 0.1% to about 25%, such as from about 1% to about 20% by weight, relative to the total weight of the composition, including all ranges and subranges therebetween.

Further Additional Components (Optional)

The compositions of the present invention can also include any additional ingredient or additive usually used in the field of cosmetic compositions, in particular eyeliners.

For example, these may be chosen from, for example, solvents, dispersants, antioxidants (such as pentaerythrityl tetra-di-t-butyl hydroxyhydrocinnamate), preservatives (such as for example phenoxyethano, sodium dehydroacetate, disodium EDTA, caprylyl glycol, and mixtures thereof), fragrances, additional thickeners or texturizers, liquid lipids/oils, additional viscosity modifiers, additional film formers, sunscreen agents, additional pigments/colorants/dyes, silica, clays, additional humectants and moisturizing agents, additional emulsifying agents (e.g. sorbitan oleate), additional structuring agents and fillers, surfactants, shine agents, additional conditioning agents, vitamins, plant extracts, additional film-formers, coalescents/plasticizers, pH modifiers/neutralizing agents, stabilizers, and mixtures thereof. A non-exhaustive listing of such ingredients is found in U.S. Pat. No. 7,879,316, the entire content of which is hereby incorporated by reference. Additional examples of additives may be found in the *International Cosmetic Ingredient Dictionary and Handbook* (9$^{th}$ ed. 2002, and subsequent editions).

Surfactants that may be employed as additional agents may be chosen from anionic, cationic, nonionic and amphoteric surfactants.

The shine agents may be chosen from silicones, alkoxylated silicones, oils, ethoxylated oils, fats, esters, transesters, hydrocarbons, quats and mixtures thereof.

Non-limiting examples of shine agents include Amodimethicone, Dimethicone, Dimethiconol, Cyclemethicone, Phenyltrimethicone, Aminopropyl Phenyltrimethicone, Trimethyl Pentaphenyl Trisiloxane, Cetyl Dimethicone, Alkyl Dimethicone, Potassium Dimethicone PEG-7 Pantheyl Phosphate, Olive oil, Jojoba oil, Apricot oil, Avocado oil, Castor oil, Lanolin, Squalane, Capric/Caprylic Triglyceride, Octyl Palmitate, Isopropyl Palmitate, Isopropyl Myristate, Mineral oil, Petrolatum, Polyquaternium-4, Polyquaternium-11, Behentrimonium Methosulfate, Benetrimonium Chloride and mixtures thereof.

If present in the composition, these additives may constitute from 2% to 30%, typically from about 3% to about 15%, and more typically about 7%, including all ranges and subranges therebetween, by weight relative to the total weight of the composition.

Cosmetic Methods

In an embodiment according to the invention, the compositions comprising a viscosity increasing system comprising at least one synthetic non-associative thickening polymer and at least one synthetic associative thickening polymer, at least one emulsifier, at least one film forming polymer, and at least one liquid fatty substance can provide a water-based gel liner having one or more the following attributes: a fresh and comfortable feel, long wear, gentle application, color intensity, and ease of removal. Accordingly, another embodiment of the invention provides a method of making up/or enhancing the appearance of eye by applying to the eyelids, topically, the composition of the present invention in a sufficient amount to make up the eyelids. The compositions may be applied to the eyelids as needed, preferably once or twice daily, and then allowed to dry before subjecting to contact such as with clothing or other objects.

The compositions according to various exemplary embodiments of the invention may also have improved and/or increased ease of removability, relative to similar compositions that are not water based. In various embodiments, ease of removability relates to ease of removing the composition from the eyelids with warm (e.g. about 50° C. or higher) water. Optionally, conventional cleansing agents such as soap or make-up remover may also be used.

As such, the disclosure also relates to methods of improving or increasing the ease of removability of eyeliner compositions by incorporating a synthetic non-associative thickening polymer, such as ammonium polyacryloyldimethyl taurate, and a synthetic associative thickening polymer, such as ammonium acryloyldimethyl taurate/steareth-8 methacrylate copolymer into said compositions as described herein.

Another embodiment of the invention relates to a method of improving at least one property selected from long wear, comfort, color intensity, ease of removal, water and/or oil-resistance, shine, adhesion, malleability, transfer resistance and ease of removal properties by incorporating in said eyeliner at least one sucrose fatty acid ester, a co-emulsifier, a viscosity increasing agent and a film forming polymer as described herein.

The composition according to the present disclosure may be manufactured by the known processes generally used in cosmetics.

When the composition of the present invention is an eyeliner, the composition may be packaged in an applicator product comprising a reservoir and a removable cap for closing the reservoir. The cap may, for example, form a leak-tight seal. An example of such an applicator is a pen-type applicator, such as the applicator described in U.S. Pat. Nos. 4,850,727 and 4,974,980, both of which are herein incorporated by reference.

The applicator assembly may also comprise a member for applying the composition to eyelid, wherein the applicator member allows the composition to be taken up and also allows the composition taken up to be deposited on the eyelids. This applicator member can be, for example, securely fastened to the cap for leak-tight closure of the assembly.

The applicator assembly may also comprise a draining member (or drainer) for the applicator member, the draining member possibly being securely fastened to the reservoir. The applicator member may for example, be an eyeliner brush that is well known to those skilled in the art. Such a brush for instance, comprises bristles extending outwardly from and parallel to core.

Unless otherwise indicated, all numbers used in the specification and claims are to be understood as being modified in all instances by the term "about," whether or not so stated. It should also be understood that the precise numerical values used in the specification, including the examples and claims, form additional embodiments of the invention, and are intended to include any ranges which can be narrowed to any to end points disclosed within the exemplary ranges and values provided. Efforts have been made to ensure the accuracy of the numerical values disclosed. However, any measured value can inherently contain certain errors resulting from the standard deviation found in its respective measuring technique.

EXAMPLES

The following Examples are intended to be non-restrictive and explanatory only, with the scope of the invention being defined by the claims.

Method of Preparation of Inventive Compositions: The Phases noted below are identified in Tables 1 and 2.

1. Water was heated to 60-70° C. with agitation using a large chopping blade (100 rpm).
2. Phase A was added while mixing with large chopping blade for 1 hr (500-900 rpm) until pigments dispersed (approx. 1 hr).
3. Phase B was added and the mixture was stirred with chopping blade (900 rpm) until a smooth texture was achieved. The temperature was then increased to 70-80° C.
4. Phase C was melted in a water bath at 80-90° C. (internal T 50-60° C.) and added slowly to the mixture in step 3. After phase C was added the resulting mixture was emulsified at 1200-1500 rpm for 20 min at 70-80° C.
5. The mixture was then cooled to less than 50° C., and a solution of Phase D was added and the composition mixed for 20 min (1200 rpm).
6. Once the mixture was homogeneous it was cooled to <30° C. and Phase E was added with mixing.

TABLE 1

Inventive Examples 1-5

| Phase | Function | INCI Name | Ex. 1 | Ex. 2 | Ex. 3 | Ex. 4 | Ex. 5 |
|---|---|---|---|---|---|---|---|
| | | | | | Amount (%) | | |
| A | Solvent (e) | water QS | 46.7 | 40.7 | 44.2 | 39.2 | 51.2 |
| | Pigment (f) | iron oxides | 20 | 20 | 20 | 20 | 20 |
| B | Emollient | butylene glycol | 3.9 | 3.9 | 3.9 | 3.9 | 3.9 |
| | Preservative | phenoxyethanol | 0.5 | 0.5 | 0.5 | 0.5 | 0.5 |
| | Preservative | sodium dehydroacetate | 0.2 | 0.2 | 0.2 | 0.2 | 0.2 |
| | | sodium hyaluronate | 0.2 | 0.2 | 0.2 | 0.2 | 0.2 |
| | Preservative | disodium EDTA | 0.2 | 0.2 | 0.2 | 0.2 | 0.2 |
| | Preservative | caprylyl glycol | 0.3 | 0.3 | 0.3 | 0.3 | 0.3 |
| | Non-associative (synthetic) (a) (I) | ammonium polyacryloyldimethyl taurate | 1.0 | 1.0 | 1.0 | 1.0 | 1.0 |
| | Associative Thickener (synthetic) (a) (II) | ammonium acryloyldimethyl aaurate/steareth-8 methacrylate copolymer | 0.5 | 0.5 | 0.5 | 0.5 | 0.5 |
| C | Emulsifier (b) (CERALUTION® H) | behenyl alcohol | 1.75 | 1.75 | 1.75 | 1.75 | 0.35 |
| | | glyceryl stearate | 1.75 | 1.75 | 1.75 | 1.75 | 0.35 |
| | | disodium ethylene dicocamide-PEG-15 disulfate ((b)) | 0.75 | 0.75 | 0.75 | 0.75 | 0.15 |
| | | glyceryl stearate citrate | 0.75 | 0.75 | 0.75 | 0.75 | 0.15 |
| D | Filler | styrene/acrylates copolymer | | 5.0 | | | 0.5 |
| | Film former (c) | divinyldimethicone/ dimethicone dopolymer (and) $C_{12-13}$ pareth-23 (and) $C_{12-13}$ pareth-3 | 3.0 | 3.0 | 3.0 | 3.0 | |

TABLE 1-continued

Inventive Examples 1-5

| Phase | Function | INCI Name | Ex. 1 | Ex. 2 | Ex. 3 | Ex. 4 | Ex. 5 |
|---|---|---|---|---|---|---|---|
| | | | | | Amount (%) | | |
| | Film former (c) | polymethylsilsesquioxane | | | | 7.5 | 7.5 |
| | Liquid Fatty Substance (d) | PEG-10 dimethicone | 1.5 | 1.5 | 1.5 | 1.5 | 0.4 |
| | Liquid Fatty Substance (d) | dimethicone (and) dimethicone/PEG-10/15 crosspolymer | 2.0 | 2.0 | 2.0 | 2.0 | 0.52 |
| | Liquid Fatty Substance (d) | phenyl trimethicone | 3.0 | 3.0 | 3.0 | 3.0 | 0.78 |
| | Liquid Fatty Substance (d) | dimethicone (and) dimethiconol | 5.0 | 5.0 | 5.0 | 5.0 | 1.3 |
| E | | alcohol denat. | 3.0 | 3.0 | 3.0 | 3.0 | |
| | | polyethylene | 2.0 | | 2.0 | 2.0 | |
| | | silica | 0.5 | | 0.5 | 0.5 | |
| | Filler | methylsilanol/silicate crosspolymer | 1.5 | | 1.5 | 1.5 | |
| | Wax (g) | microcrystalline wax | | | | | 2.5 |
| | Wax (g) | ozokerite | | | | | 2.5 |
| C | Wax (g) | beeswax | | 5.0 | | | 5.0 |
| | Wax (g) | candelilla wax | | | | | |
| | Film former (c) | poly $C_{10-30}$ alkyl acrylate | | | 2.5 | | |
| | Viscosity (Rheomat, Method B) | | 13.2 Pa·s | 23.6 Pa·s | 15.1 Pa·s | 19.1 Pa·s | 55 Pa·s |

TABLE 2

Examples 6-12

| Phase | Function | INCI Name | Ex. 6 Comparative | Ex. 7 Comparative | Ex. 8 | Ex. 9 | Ex. 10 | Ex. 11 | Ex. 12 |
|---|---|---|---|---|---|---|---|---|---|
| | | | | | Amount (%) | | | | |
| A | Solvent (e) | water QS | 46.7 | 47.2 | 46.7 | 47.2 | 46.7 | 46.7 | 46.7 |
| | Pigment (f) | iron oxides | 20 | 20 | 20 | 20 | 20 | 20 | 20 |
| B | Emollient | butylene glycol | 3.9 | 3.9 | 3.9 | 3.9 | 3.9 | 3.9 | 3.9 |
| | Preservative | Phenoxyethanol | 0.5 | 0.5 | 0.5 | 0.5 | 0.5 | 0.5 | 0.5 |
| | Preservative | sodium dehydroacetate | 0.2 | 0.2 | 0.2 | 0.2 | 0.2 | 0.2 | 0.2 |
| | | sodium hyaluronate | 0.2 | 0.2 | 0.2 | 0.2 | 0.2 | 0.2 | 0.2 |
| | Preservative | disodium EDTA | 0.2 | 0.2 | 0.2 | 0.2 | 0.2 | 0.2 | 0.2 |
| | Preservative | caprylyl glycol | 0.3 | 0.3 | 0.3 | 0.3 | 0.3 | 0.3 | 0.3 |
| | Non-associative (synthetic) (a) (I) | ammonium polyacryloyldimethyl taurate | 1.5 | 1.0 | 0 | 0 | 0.5 | 0 | 0.5 |
| | Associative Thickener (synthetic) (a) (II) | ammonium acryloyldimethyl taurate/steareth-8 methacrylate copolymer | | | 1.5 | 1.0 | 1.0 | 1.5 | 1.0 |
| C | Emulsifier (b) | behenyl alcohol | 1.75 | 1.75 | 1.75 | 1.75 | 1.75 | | 1.75 |
| | | glyceryl stearate | 1.75 | 1.75 | 1.75 | 1.75 | 1.75 | | 1.75 |
| | (CERALUTION ® H) | disodium ethylene dicocamide-PEG-15 disulfate ((b)) | 0.75 | 0.75 | 0.75 | 0.75 | 0.75 | | 0.75 |
| | | glyceryl stearate citrate | 0.75 | 0.75 | 0.75 | 0.75 | 0.75 | | 0.75 |
| | Emulsifier (b) | cetyl alcohol | | | | | | 5 | |
| | Film former (c) | divinyldimethicone/Dimethicone copolymer (and) $C_{12-13}$ pareth-23 (and) $C_{12-13}$ pareth-3 | 3.0 | 3.0 | 3.0 | 3.0 | 3.0 | 3.0 | 3.0 |
| D | Film former (c) | polymethylsilsesquioxane | | | | | | | 7.5 |
| | Liquid Fatty Substance (d) | PEG-10 dimethicone | 1.5 | 1.5 | 1.5 | 1.5 | 1.5 | 1.5 | 1.5 |
| | Liquid Fatty Substance (d) | dimethicone (and) dimethicone/PEG-10/15 drosspolymer | 2.0 | 2.0 | 2.0 | 2.0 | 2.0 | 2.0 | 2.0 |

TABLE 2-continued

Examples 6-12

| Phase | Function | INCI Name | Ex. 6 Comparative | Ex. 7 Comparative | Ex. 8 | Ex. 9 | Ex. 10 | Ex. 11 | Ex. 12 |
|---|---|---|---|---|---|---|---|---|---|
| | | | | | Amount (%) | | | | |
| | Liquid Fatty Substance (d) | phenyl trimethicone | 3.0 | 3.0 | 3.0 | 3.0 | 3.0 | 3.0 | 3.0 |
| | Liquid Fatty Substance (d) | dimethicone (and) dimethiconol | 5.0 | 5.0 | 5.0 | 5.0 | 5.0 | 5.0 | 5.0 |
| E | Preservative | alcohol denat. | 3.0 | 3.0 | 3.0 | 3.0 | 3.0 | 3.0 | 3.0 |
| | Filler | polyethylene | 2.0 | 2.0 | 2.0 | 2.0 | 2.0 | 2.0 | 2.0 |
| | Filler | silica | 0.5 | 0.5 | 0.5 | 0.5 | 0.5 | 0.5 | 0.5 |
| | Filler | methylsilanol/ Silicate crosspolymer | 1.5 | 1.5 | 1.5 | 1.5 | 1.5 | 1.5 | 1.5 |
| | Viscosity (Rheomat, Method B) | | 13.2 Pa·s | 8.7 Pa·s | 15.6 Pa·s | 9.5 Pa·s | 13.7 Pa·s | Ca. 15.0 Pa·s | 18.9 Pa·s |

Rheology:

The rheology of the compositions of the invention was compared with that of two commercially-available anhydrous comparator eye liner compositions. The comparator compositions were as follows:

Comparator A: Commercial anhydrous gel eyeliner containing approximately 20% more pigments than the inventive compositions of Examples 1 and 2. Key ingredients are: Trimethylsiloxysilicate, Cyclopentasiloxane, Isododecane, Cyclohexasiloxane, Ceresin, Caprylyl Methicone, Silica Silylate, Disteardimonium Hectorite, Trieth-Oxycaprylylsilane, Talc, Synthetic Fluorphlogopite, Propylene Carbonate, BHT and Tin Oxide.

Comparator B: Commercial anhydrous gel eyeliner known for having a creamy texture. Key ingredients are: Isododecane, cyclopentasiloxane, polyethylene, Barium sulfate, trimethylsiloxysilicate, disteardimonium hectorite, propylene carbonate, lecithin, phenyl trimethicone, ethylhexylglycerin, hydrogenated polyisobutene and methicone.

The rheology of the compositions was measured as follows: Data was collected on a TA Instrument AR G2 Rheometer. All values were measured with a 20 mm 2° cone (990901) in continuous mode unless otherwise stated (Method A).

Parameters:
Test type: Continuous mode
Ramp: shear rate 1/s, from 0.01-1000 1/s
Duration: 10 minutes
Mode: log
Sample: points per decade=5
Temperature: 25° C.

Values:
Viscosities (Pa*s) were reported at the onset of the run at a low shear rate (0.015 s$^{-1}$) and at the end of the run at a high shear rate (990 s$^{-1}$).

The results of the rheological comparisons are summarized below in Table 3.

TABLE 3

| Composition | Viscosity[1] (Pa * s @ 0.015 1/s) (low shear) | Viscosity[1] (Pa * s@ 990 1/s) (high shear) | Slope[2] |
|---|---|---|---|
| Comparator A | 49330 | 0.36 | −1.0 |
| Comparator B | 3829 | 0.19 | −0.86 |
| Composition of Example 1 | 7470 | 1.32 | −0.74 |
| Composition of Example 2 | 8404 | 0.93 | −0.76 |
| Composition of Example 3 | 9590 | 1.24 | −0.78 |
| Composition of Example 4 | 4099 | 0.69 | −0.77 |
| Composition of Example 5 | 15740 | 1.31 | −0.87 |
| Comparative Composition-Example 6 | 2913 | 0.94 | −0.69 |
| Comparative Composition-Example 7 | 2746 | 0.69 | −0.82 |
| Composition of Example 8 | 13560 | 0.02 | −0.95 |
| Composition of Example 9 | 25530 | 0.04 | −1.0 |
| Composition of Example 10 | 6451 | 0.57 | −0.77 |
| Composition of Example 11 | 10920 | 0.23 | −0.98 |
| Composition of Example 12 | 4099 | 0.28 | −0.77 |

[1]Using method A
[2]Slope refers to the slope of a viscosity (Pa · s) versus shear rate (1/s) graph The steady shear flow of the inventive water-based compositions were compared to anhydrous Competitors A and B. The inventive compositions comprising the indicated components in particular ratios provided varying shear thinning profiles. The rheological profile was optimized to provide optimal control of pickup (low shear viscosity) and application (high shear viscosity) of the compositions. Inventive compositions with low "low shear" viscosities (2000 to 10000 Pa*s) exemplify products that have a creamier texture, comparable to Competitor B and are picked up with a dip mechanism. Examples with higher "low shear" viscosities (10000-40000 Pa*s) exemplify products that are similar to soft solids and are picked up with a mechanism typically used for anhydrous gel eyeliners.

As is shown in Table 3, inventive compositions that have a ratio of a(i)/a(ii) of 2:1 or greater (Examples 1-4) yield solvent-free, water-based gels having "low shear" viscosities ranging from 2000-10000 Pa*s, which is comparable to Competitor B without the use of waxes. Thus these water-based compositions (Examples 1-4) have creamier textures such as those exemplified by Competitor B, which is picked up by dip mechanism. The "low shear" viscosities for Examples 6-7, which lack a(ii) are lower still, suggesting these are more fluid creams. The "low shear" viscosities of formulas with a ratio of a(i)/a(ii) greater than or equal to 2:1 can be increased and made to approach those of Competitor A with the addition of waxes (Example 5). In contrast, inventive compositions that have a ratio of a(i)/a(ii) less than 1:1 (Examples 8-12) achieved in the absence of waxes a higher range of "low shear" viscosities from 4000 to 30000 Pa*s approaching the viscosity of Competitor A. This profile provides consumers with cosmetic products in aqueous conditions that can be picked up in a similar fashion to commercial anhydrous gel eyeliner formulas.

High shear viscosities on a rheological graph represent the application region of a product (such as the application of a cosmetic on skin). As shown with Examples 1-12, the inventive compositions exemplified have "high shear" viscosities ranging from 0.01 to 1.4 Pa*s. More specifically, by attenuating the ratio of a(i)/a(ii) in the formula (Examples 8 to 12) the inventive compositions were able to achieve "high shear" viscosities comparable to Competitor A and B, suggesting comparable to better application.

The slope of the viscosity (Pa*s) versus shear rate (1/s) graph gives an indication of shear thinning properties, which also impacts application. The slopes of the viscosity (Pa*s) versus shear rate (1/s) graph for anhydrous wax containing formulas of Competitor A and B are from about −0.86 to about −1.0. Examples 7-9, and 11 have comparable shear thinning properties (close slopes) to anhydrous Competitors A and B, but achieve this in an aqueous system without the use of waxes. It is noteworthy that for Examples 8-9 and 11 this is achieved without the aid of soft low melting waxes that would otherwise melt on the skin, as those used in Competitor A and B.

Test for Color Intensity: Wet Mass Tones LAB Evaluation Procedure:

The compositions of the invention and Comparator A were applied to Fisher premium plain glass slides (3" by 1" by 1 mm thick). The color intensity of the film formed by each composition was measured using a Data Color 600 Colorimetric Spectrophotometer for wet mass tone. The colorimetric spectrophotometer measures the entire visible spectrum of light being reflected from a sample in 5 nanometer increments (generally perceptible 400-700 nanometers wavelength—each wavelength corresponding to a color, like a rainbow). The reflectance data from the 31 data points can be mathematically calculated to provide a more understandable result giving number values for Lightness (white to black), Chroma (the amount of color) and Hue (the shade of color). Additional values can also be calculated as "a" for the value of red or green and "b" for the value yellow or blue.

Color Scales:

The color scales used for this test were the Hunter L,a,b and the CIE L*,a*,b* scales. These are 3-dimensional scales. Both are based on the opponent-colors theory that states that the red, green and blue human eye cone responses are re-mixed into black-white, red-green, and yellow-blue, opponent coders as they move up the optic nerve to the brain.

The L,a,b type of scales simulate this as:

_L (lightness) axis—0 is black, 100 is white
_a (red-green) axis—positive values are red; negative values are green and 0 is neutral
_b (yellow-blue) axis—positive values are yellow; negative values are blue and 0 is neutral
_C (chroma saturation)—0 is no color value. Numbers can only be positive numbers and indicate greater and greater amounts of color.
_h (hue) axis—0° is red, 90° is yellow, 180° is green and 270° is blue.

All colors that can visually be perceived can be measured in L,a,b. This test specifically refers to the L values as it is the measure of black versus white. As 0 is black, the lower the L value, the darker the color. Hue is measured as h* which is a measure of the degree of the angle from red.

The results of this test are provided below in Table 4.

TABLE 4

| L* Wet Mass Tone Measurements | |
|---|---|
| Composition | L* |
| Comparator A (contains 19% more pigments than inventive compositions) | 28.44 |
| Example 1 | 27.82 |
| Example 2 | 28.27 |

As can be seen from Table 4, the inventive compositions of Examples 1 and 2 yield comparably dark eyeliners to those of the Comparator A (same color intensity) even while Comparator A contains approximately 20% more pigments than the compositions of the invention.

Eyelid Lash Line Test:
Procedure for Determination of Glide Across the Eyelid:
Brush was dipped into product to cover the entire brush. Brush was then placed either on outside corner (or inside corner) of eyelid and carefully swiped across the eyelid. The percent across the eyelid was then determined as less than 50% across, 50% across or greater than 80% across.

Definition of Glide Percentages:
<50% across=less than 50% of the eyelid along the lash line was covered with product
50% across=50% of the eyelid along the lash line was covered with product
>80% across=>80% of the eyelid along the lash line was covered with product The results of this test are described below in Table 5.

TABLE 5

| Composition | Percentage of the eyelid covered by product after 1-2 strokes |
|---|---|
| Comparator A | >80% |
| Example 1 | >80% (outside corner to inside corner) |
| Example 2 | >80% (outside corner to inside corner) |

As is shown in Table 5, the water-based compositions of the invention provide comparable coverage and application across the eyelid (glide) to that of the commercially-available anhydrous Comparator A composition.

Gloss Test:
Procedure for Test:
The gloss of the inventive compositions as well as of Comparator A was measured using a BYK Gardner micro glossmeter and following the ASTM Standard Test Method for determining Gloss as described at http://www.opbpak.com/ASTM/D2457-03.pdf or http://www.astm.org/Standards/D523.htm.

The results of this test are reported below in Table 6.

Gloss measurements were determined from 3 mil drawdowns of formulas on Laneta Black and White draw down cards. "Drawdown" is a term of art in the cosmetic industry.

In this procedure, the gels were scooped and spread evenly on the cards using a metal "drawdown" bar. Once the films dried, the shine of the resulting films was measured on a BYK Gardner micro glossmeter. The measurements are reported in gloss units (GU) which represent the ratio of reflected to incident light of the films compared to that for a standard. Low gloss is a GU measurement less than 10 at a measurement angle of 85 degrees. The results in Table 6 are an average of three trials.

TABLE 6

Results of Gloss Test

| Composition | GU Values at 85° average (st. dev, n = 3) |
|---|---|
| Comparator A | Could not obtain drawdown |
| Example 1 | 1.3 (0.7) |
| Example 2 | 6.1 (0.6) |

Table 6 above shows that the inventive compositions yielded a cosmetic product that was not glossy (had gloss values less than 10 GU). This is desirable for eyeliners as consumers prefer non-shiny, natural looking eyeliners.

What is claimed is:

1. A water-based gel cosmetic composition comprising:
   (a) a viscosity increasing system comprising (I) at least one synthetic non-associative thickening polymer comprising acryloyldimethyltaurate; and (II) at least one synthetic associative thickening polymer selected from the group consisting of ammonium acryloyldimethyltaurate/steareth-8 methacrylate copolymer, ammonium acryloyldimethyltaurate/laureth-7 methacrylate copolymer, and mixtures thereof;
   (b) at least one emulsifier selected from the group consisting of glycerol esters, oxyalkylenated esters, gemini surfactants, and mixtures thereof;
   (c) at least one film forming polymer;
   (d) at least one liquid fatty substance;
   (e) water;
   (f) optionally a pigment; and
   (g) optionally at least one wax;
   wherein the composition has a viscosity at 25° C. of from about 2,000 Pa·s to about 90,000 Pa·s at low shear rate.

2. The composition of claim 1 wherein the ratio of the at least one synthetic non-associative thickening polymer (a)(I) to the at least one synthetic associative thickening polymer (a)(II) is greater than 1:1.

3. The composition of claim 2 wherein the viscosity increasing system is present in an amount of from about 0.11% to about 4%, by weight, relative to the total weight of the composition.

4. The composition of claim 3 wherein the viscosity increasing system (a) comprises (I) from about 0.01% to about 2.0% by weight of at least one synthetic non-associative thickening polymer; and (II) from about 0.1% to about 2.0% by weight of at least one synthetic associative thickening polymer, by weight, relative to the total weight of the composition.

5. The composition of claim 4 wherein the at least one emulsifier (b) is present in an amount of from about 0.1% to about 7.5%, by weight, relative to the total weight of the composition.

6. The composition of claim 5 wherein the at least one film forming polymer (c) is present in an amount of from about 0.1% to about 50%, by weight, relative to the total weight of the composition.

7. The composition of claim 6 wherein the liquid fatty substance (d) is present in an amount of from about 0.1% to about 30%, by weight, relative to the total weight of the composition.

8. The composition of claim 7 wherein the water (e) is present in an amount of from about 5% to about 60%, by weight, relative to the total weight of the composition.

9. The composition of claim 4 wherein h ratio of the at least one synthetic non-associative thickening polymer (a)(I) to the at least one synthetic associative thickening polymer (a)(II) is from about 1.5:1 to about 3:1.

10. The composition of claim 9 wherein the at least one emulsifier (b) is selected from glycerol esters, oxyalkylenated esters, and mixtures thereof.

11. The composition of claim 9 wherein the at least one emulsifier (b) is a gemini surfactant.

12. The composition of claim 2 wherein the at least one synthetic non-associative thickening polymer (a)(I) is present in an amount of about 1% by weight, the at least one synthetic associative thickening polymer (a)(II) is present in an amount of about 0.5% by weight, the at least one emulsifier (b) is present in an amount of about 0.75% by weight, the at least one film former (c) is present n an amount from about 2.0% to about 10.5% by weight, the at least one liquid fatty substance (d) is present in an amount of about 11.5% by weight, and water (e) is present in an amount of from about 40% to about 55% by weight, relative to the weight of the final composition.

13. The composition of claim 10 comprising wax.

14. A water-based gel cosmetic composition comprising:
   (a) a viscosity increasing system comprising (I) at least one synthetic non-associative thickening polymer comprising acryloyldimethyltaurate; and (II) at least one synthetic associative thickening polymer selected from the group consisting of ammonium acryloyldimethyltaurate/steareth-8 methacrylate copolymer, ammonium acryloyldimethyltaurate/laureth-7 methacrylate copolymer, and mixtures thereof;
   (b) at least one emulsifier selected from the group consisting of glycerol esters, oxyalkylenated esters, gemini surfactants, and mixtures thereof;
   (c) of at least one film forming polymer;
   (d) at least one liquid fatty substance;
   (e) water;
   (f) optionally a pigment; and
   (g) optionally at least one wax;
   wherein the ratio of the t least one synthetic non-associative thickening polymer (a)(I) to the at least one synthetic associative thickening polymer (a)(II) is less than or equal to 1:1; all percentages and ratios being based on the total weight of the composition.

15. The composition of claim 14 wherein the viscosity increasing system (a) s present in an amount of from about 0.11% to about 4%, by weight, relative to the total weight of the composition.

16. The composition of claim 15 wherein the at least one synthetic non-associative thickening polymer (a)(II) is present in an amount of from about 0.0% to about 2.0%, by weight, relative to the total weight of the composition.

17. The composition of claim 16 wherein the at least one emulsifier (b) is present in an amount of from about 0.4% to about 7.5%, by weight, relative to the total weight of the composition.

18. The composition of claim 17 wherein the at least one film forming polymer (c) is present in an amount of from about 0.1% to about 50%, by weight, relative to the total weight of the composition.

19. The composition of claim 18 wherein the at least one liquid fatty substance (d) is present in an amount of from about 0.1% to about 30%, by weight, relative to the total weight of the composition.

20. The composition of claim 19 wherein the water (e) is present in an amount of from about 5% to about 60%, by weight, relative to the total weight of the composition.

21. The composition of claim 14 wherein ratio of the at least one synthetic non-associative thickening polymer (a)(I) to the at least one synthetic associative thickening polymer (a)(II) is from about 0:0.5 to about 1:3.

22. The composition of claim 20 having a viscosity of from about 3,000 Pa·s to about 90,000 Pa·s at low shear rate.

23. The composition of claim 9 wherein the at least one emulsifier (b) is selected from glycerol esters, oxyalkylenated esters, and mixtures thereof.

24. The composition of claim 21 wherein the at least one synthetic non-associative thickening polymer (a)(I) is present in an amount of from about 0% to about 1.5% by weight, the at least one synthetic associative thickening polymer (a)(II) is present in an amount of from about 1.0% to about 1.5% by weight, the at least one emulsifier (b) is present in an amount of about 0.75% by weight, the at least one film former (c) is present in an amount from about 3.0% to about 10.5% by weight, the at least one liquid fatty substance (d) is present in an amount of about 11.5% by weight, and water s present in an amount of from about 46% to about 48% by weight, relative to the weight of the final composition.

25. The composition of claim 22 comprising wax.

26. A kit for making up the eyes comprising a pen-type applicator containing the composition of claim 1.

27. A method of making up or enhancing the appearance of the eye by applying to the eyelids, topically, a composition according to claim 1.

28. The composition of claim 1, wherein the at least one synthetic associative thickening polymer is ammonium acryloyldimethyltaurate/steareth-8 methacrylate.

29. The composition of claim 28, wherein the at least one synthetic non-associative thickening polymer is selected from the group consisting of sodium acryloyldimethyltaurate/VP crosspolymer, ammonium acryloyl dimethyltaurate/carboxyethyl acrylate crosspolymer, ammonium polyacryloyldimethyl taurate, ammonium acryloyldimethyltaurate/vinyl formamide copolymer, ammonium polyacryloyldimethyl taurate/ammonium polyacryldimethyltauramide, ammonium acryloyldimethyltaurate/VP copolymer, and mixtures thereof.

30. The composition of claim 1, wherein the at least one synthetic associative thickening polymer is ammonium acryloyldimethyltaurate/laureth-7 methacrylate copolymer.

31. The composition of claim 30, wherein the at least one synthetic non-associative thickening polymer is selected from the group consisting of sodium acryloyldimethyltaurate/VP crosspolymer, ammonium acryloyl dimethyltaurate/carboxyethyl acrylate crosspolymer, ammonium polyacryloyldimethyl taurate, ammonium acryloyldimethyltaurate/vinyl formamide copolymer, ammonium polyacryloyldimethyl taurate/ammonium polyacryldimethyltauramide, ammonium acryloyldimethyltaurate/VP copolymer, and mixtures thereof.

* * * * *

UNITED STATES PATENT AND TRADEMARK OFFICE
CERTIFICATE OF CORRECTION

PATENT NO. : 9,517,188 B2
APPLICATION NO. : 14/221646
DATED : December 13, 2016
INVENTOR(S) : Christine Marie Crane et al.

Page 1 of 1

It is certified that error appears in the above-identified patent and that said Letters Patent is hereby corrected as shown below:

In the Claims

Column 38, Line 8, "The composition of claim 4 wherein h ratio" should read --The composition of claim 4, wherein the ratio--;
 Line 23, "(c) is present n an" should read --(c) is present in an--;
 Line 47, "wherein the ratio of the t least one" should read --wherein the ratio of the at least one--;
 Line 53, "(a) s present in an amount" should read --(a) is present in an amount--;
 Line 57, "synthetic non-associative thickening" should read --synthetic associative thickening--;
 Line 58, "about 0.0% to" should read --about 0.01% to--.

Column 39, Line 26, "and water" should read --and water (e)--;
 Line 27, "s present in an amount" should read --is present in an amount--.

Signed and Sealed this
Twenty-seventh Day of February, 2018

Andrei Iancu
*Director of the United States Patent and Trademark Office*